United States Patent
Lu et al.

(10) Patent No.: US 9,506,063 B2
(45) Date of Patent: Nov. 29, 2016

(54) SIRNA COMPOSITIONS AND METHODS FOR TREATMENT OF HPV AND OTHER INFECTIONS

(71) Applicants: Alan Y. Lu, Lutherville-Timonium, MD (US); Patrick Y. Lu, Rockville, MD (US); David M. Evans, North Potomac, MD (US); John J. Xu, Germantown, MD (US)

(72) Inventors: Alan Y. Lu, Lutherville-Timonium, MD (US); Patrick Y. Lu, Rockville, MD (US); David M. Evans, North Potomac, MD (US); John J. Xu, Germantown, MD (US)

(73) Assignee: Sirnaomics, Inc., Gaithersburg, MD (US)

( * ) Notice: Subject to any disclaimer, the term of this patent is extended or adjusted under 35 U.S.C. 154(b) by 0 days.

(21) Appl. No.: 13/752,568

(22) Filed: Jan. 29, 2013

(65) Prior Publication Data
US 2013/0345284 A1 Dec. 26, 2013

Related U.S. Application Data

(63) Continuation-in-part of application No. PCT/US2011/045884, filed on Jul. 29, 2011.

(60) Provisional application No. 61/369,067, filed on Jul. 29, 2010.

(51) Int. Cl.
*C12N 15/113* (2010.01)

(52) U.S. Cl.
CPC ....... *C12N 15/1131* (2013.01); *C12N 2310/14* (2013.01); *C12N 2310/17* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 7,199,109 B2 | 4/2007 | Pal et al. | |
| 8,541,568 B2 | 9/2013 | Yan et al. | |
| 2005/0176024 A1 | 8/2005 | McSwiggen et al. | |
| 2006/0058252 A1* | 3/2006 | Clawson ................ | A61K 31/19 514/44 A |
| 2006/0134787 A1 | 6/2006 | Zamore et al. | |
| 2007/0003519 A1 | 1/2007 | Lu et al. | |
| 2007/0185049 A1* | 8/2007 | Jadhav .................. | C07H 21/02 514/44 A |
| 2007/0197460 A1 | 8/2007 | Fougerolles et al. | |
| 2008/0171025 A1* | 7/2008 | Mixson ...................... | 424/93.21 |
| 2008/0214485 A1* | 9/2008 | McMillan ............. | C12N 15/111 514/44 A |
| 2008/0241198 A1 | 10/2008 | Liu et al. | |
| 2008/0279920 A1 | 11/2008 | Tang et al. | |
| 2008/0287385 A1 | 11/2008 | Harel-Bellan et al. | |
| 2009/0012022 A1* | 1/2009 | Milner ................... | C12N 15/111 514/44 R |
| 2009/0247607 A1 | 10/2009 | Benson et al. | |
| 2010/0062051 A1 | 3/2010 | Shin et al. | |
| 2010/0319074 A1 | 12/2010 | Lu et al. | |
| 2012/0071540 A1 | 3/2012 | Lu et al. | |
| 2013/0225655 A1 | 8/2013 | Lu et al. | |

FOREIGN PATENT DOCUMENTS

| | | | |
|---|---|---|---|
| CN | 101182517 A | * | 5/2008 |
| WO | WO 0147496 A1 | | 7/2001 |
| WO | WO 03040399 A2 | | 5/2003 |
| WO | WO 03070918 A2 | | 8/2003 |
| WO | WO 03090719 A1 | | 11/2003 |
| WO | WO 2005076999 A2 | | 8/2005 |

OTHER PUBLICATIONS

English translation of CN 101182517, 18 pages.*
Barik, Sailen, "Control of nonsegmented negative-strand RNA virus replication by siRNA," Virus Research, vol. 102, 2004, pp. 27-35.
Bitko, Vira, et al., "Phenotypic silencing of cytoplasmic genes using sequence-specific double-stranded short interfering RNA and its application in the reverse genetics of wild type negative-strand RNA viruses," BMC Microbiology, vol. 1, No. 34, Dec. 20, 2001, pp. 1-11.
De Wolf, Holger, et al., "Effect of Cationic Carriers on the Pharmacokinetics and Tumor Localization of Nucleic Acids after Intravenous Administration," International Journal of Pharmaceutics, 331, 2007, pp. 167-175.
Leng, Qixin, et al, "Highly Branched HK Peptides Are Effective Carriers of siRNA," The Journal of Gene Medicine, Jul. 2005, pp. 977-986.
Pickering, Lulu, "Progress in RNA-based therapeutics," Spectrum Drug Discovery and Design, Decision Resources, Inc., Waltham, Massachusetts, Aug. 4, 2005, pp. 6-1 to 6-20.
Lung, Mandy, The use of human papillomavirus promoter to target cervical cancer cells. PhD Thesis, University of New South Wales, Sidney, Australia, Aug. 2008 [online]. (Retrieved from the internet on Feb. 3, 2012]. Entire document.
International Search Report and Written Opinion of the International Searching Authority/US on International App. No. PCT/US2011/045884 (WO 2012/016139) of Sirnaomics, Inc., Feb. 16, 2012.

* cited by examiner

*Primary Examiner* — Tracy Vivlemore
(74) *Attorney, Agent, or Firm* — Geoffrey M. Karny

(57) ABSTRACT

The invention provides siRNA compositions that (1) interfere with viral replication of human papillomavirus (HPV), herpes simplex virus (HSV), and human immunodeficiency virus (HIV) in mucosal tissues, such as genital tissues, and (2) treat fungal infections. The compositions include siRNA molecules that target HPV, complexed with a dendrimer that treats and prevents genital herpes (HSV) and HIV. The compositions also include siRNA molecules that target HPV, complexed with a histidine-lysine (HK) polymer that treats and prevent fungus infection. The combined formulations of siRNA and dendrimer provide treatment of the infections from HPVs, HSVs, and HIVs. The combined formulations of siRNA and HK polymer provide treatment of HPVs and fungus infections.

27 Claims, 14 Drawing Sheets gcatgaatatatgttggatctgca CPRE7-36

[highlighted sequence] atgcatggagatacacctacattgcatgaa ... gatctctact gcatgaatatatgttagatttgcaa 16E7-36

[highlighted sequence] gttatgagcaattaaatgacagctcagaggaggaggatgaatagatggtccagctggacaagcagaacc gcccactacaacatgtgaccttt CRPE7-38 ggacagagcccactacaacatgt CRPE7-37

[highlighted sequence] ggacagagcc ... tttgttgcaagtgactctacgctcggttgtcgtacaaagcacacacgtag ggacagagcccattacaatattgta 16E7-37 gcccattacaatattgtaacctttt 16E7-38 gcacctgggcatctgtgcccat CRPE7-45 cctgctgatgggcacctgggcat CRPE7-44 ggaagacctgctgatgggcacct CRPE7-43

[highlighted sequence] acattcgtacttgaagac ... gcccatgttctagaaaccataa ggaagacctgttaatgggcacacta 16E7-43 cctgttaatgggcacactaggaatt 16E7-44 gcacactaggaattgtgtgccccat 16E7-45

| siRNA | Target | CRV/wt | HPV/CRV-E6I/1I7 | HPV/CRV-E6I/8I7 | HPV/CRV-E7 |
|---|---|---|---|---|---|
| CPRV37 | HPV16E7 /49-57 | Smaller | Smaller | Smaller | Smaller |
| CRPV43 | | No effect | Smaller | Smaller | No effect |
| CRPV44 | HPV16E7 /82-90 | No effect | No effect | Smaller | No effect |
| CRPV45 | | No effect | No effect | Smaller | Smaller |

Figure 11

SEQUENCE LISTING

<160> NUMBER OF SEQ ID NOS: 171

<210> SEQ ID NO 1
<211> LENGTH: 23
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 1

Lys Lys Lys Lys His Lys His His Lys His His Lys His His Lys His
1               5                   10                  15

His Lys His His Lys His Lys
            20

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Cys Arg Gly Asp Met Phe Gly Cys Ala
1               5                   10

<210> SEQ ID NO 3
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Tyr Thr Ile Trp Met Pro Glu Asn Pro Arg Pro Gly Thr Pro Cys Asp
1               5                   10                  15

Ile Phe Thr Asn Ser Arg Gly Lys Arg Ala Ser Asn Gly
            20                  25

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Asp Tyr Glu Leu Met Asp Leu Leu Ala Tyr Leu
1               5                   10

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggaatccata tgctgtatgt                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 6
ctacgtgttc ttgatgatct                                                    20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
caacattaga acagcaatac                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
atgatctgca acaagacata                                                    20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attgcatgaa tatatgttag att                                                23

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacaattcct agtgtgccca tta                                                23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
acacttcact gcaagacata                                                    20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12

```
ccatacacag agtctgaata                                               20
```

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

```
agacagtatt ggaacttaca                                               20
```

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

```
tacacagagt ctgaataatg                                               20
```

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15

```
tgcatttaga gccccaa                                                  17
```

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

```
cacaaaggac agggtgt                                                  17
```

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17

```
cacaacaaau gugaaugcag accaa                                         25
```

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
uuggucugca uucacauuug uugug 25

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
ucgagacccu gguggacaut t 21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
auguccacca gggucucgat t 21

<210> SEQ ID NO 21
<211> LENGTH: 25
<212> TYPE: DNA
<213> ORGANISM: Human papillomavirus

<400> SEQUENCE: 21
gcatggagat acacctacat tgcat 25

<210> SEQ ID NO 22
<211> LENGTH: 25
<212> TYPE: DNA
<213> ORGANISM: Human papillomavirus

<400> SEQUENCE: 22
ggacagagcc cattacaata ttgta 25

<210> SEQ ID NO 23
<211> LENGTH: 25
<212> TYPE: DNA
<213> ORGANISM: Human papillomavirus

<400> SEQUENCE: 23
gcaagtgtga ctctacgctt cggtt 25

<210> SEQ ID NO 24
<211> LENGTH: 25
<212> TYPE: DNA
<213> ORGANISM: Human papillomavirus

<400> SEQUENCE: 24
gcgtacaaag cacacacgta gacat 25

<210> SEQ ID NO 25
<211> LENGTH: 25
<212> TYPE: DNA
<213> ORGANISM: Human papillomavirus

```
<400> SEQUENCE: 25
cgtacaaagc acacacgtag acatt                                          25

<210> SEQ ID NO 26
<211> LENGTH: 25
<212> TYPE: DNA
<213> ORGANISM: Human papillomavirus

<400> SEQUENCE: 26
gcacacacgt agacattcgt acttt                                          25

<210> SEQ ID NO 27
<211> LENGTH: 25
<212> TYPE: DNA
<213> ORGANISM: Human papillomavirus

<400> SEQUENCE: 27
ggaagacctg ttaatgggca cacta                                          25

<210> SEQ ID NO 28
<211> LENGTH: 25
<212> TYPE: DNA
<213> ORGANISM: Human papillomavirus

<400> SEQUENCE: 28
cctgttaatg ggcacactag gaatt                                          25

<210> SEQ ID NO 29
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gcaugaauau auguuggauc ugca                                           24

<210> SEQ ID NO 30
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
ggacagagcc cacuacaaca ucgu                                           24

<210> SEQ ID NO 31
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 31
gcccacuaca acaucgugac cuuuu                                          25

<210> SEQ ID NO 32
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 32
ggaagaccug cugaugggca cccu                                                24

<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
ccugcugaug ggcacccugg gcau                                                24

<210> SEQ ID NO 34
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gcacccuggg cauccugugc cccau                                               25

<210> SEQ ID NO 35
<211> LENGTH: 25
<212> TYPE: RNA
<213> ORGANISM: Human papillomavirus

<400> SEQUENCE: 35
gcauggaccu aaggcaacau ugcaa                                               25

<210> SEQ ID NO 36
<211> LENGTH: 25
<212> TYPE: RNA
<213> ORGANISM: Human papillomavirus

<400> SEQUENCE: 36
gguugaccuu cuaugucacg agcaa                                               25

<210> SEQ ID NO 37
<211> LENGTH: 25
<212> TYPE: RNA
<213> ORGANISM: Human papillomavirus

<400> SEQUENCE: 37
gcaauuaagc gacucagagg aagaa                                               25

<210> SEQ ID NO 38
<211> LENGTH: 25
<212> TYPE: RNA
<213> ORGANISM: Human papillomavirus

<400> SEQUENCE: 38
cgaugaaaua gauggaguua aucau                                               25

<210> SEQ ID NO 39
<211> LENGTH: 25
<212> TYPE: RNA
<213> ORGANISM: Human papillomavirus
```

```
<400> SEQUENCE: 39
cgagccgaac cacaacguca cacaa                                     25

<210> SEQ ID NO 40
<211> LENGTH: 25
<212> TYPE: RNA
<213> ORGANISM: Human papillomavirus

<400> SEQUENCE: 40
gccagaauug agcuaguagu agaaa                                     25

<210> SEQ ID NO 41
<211> LENGTH: 25
<212> TYPE: RNA
<213> ORGANISM: Human papillomavirus

<400> SEQUENCE: 41
gcucagcaga cgaccuucga gcauu                                     25

<210> SEQ ID NO 42
<211> LENGTH: 25
<212> TYPE: RNA
<213> ORGANISM: Human papillomavirus

<400> SEQUENCE: 42
gcuguuucug aacacccugu ccuuu                                     25

<210> SEQ ID NO 43
<211> LENGTH: 25
<212> TYPE: DNA
<213> ORGANISM: Human papillomavirus

<400> SEQUENCE: 43
cccacaggag cgacccagaa agtta                                     25

<210> SEQ ID NO 44
<211> LENGTH: 25
<212> TYPE: DNA
<213> ORGANISM: Human papillomavirus

<400> SEQUENCE: 44
cgacccagaa agttaccaca gttat                                     25

<210> SEQ ID NO 45
<211> LENGTH: 25
<212> TYPE: DNA
<213> ORGANISM: Human papillomavirus

<400> SEQUENCE: 45
ccacagttat gcacagagct gcaaa                                     25

<210> SEQ ID NO 46
<211> LENGTH: 25
<212> TYPE: DNA
<213> ORGANISM: Human papillomavirus

<400> SEQUENCE: 46
cgacgtgagg tatatgactt tgctt                                     25

<210> SEQ ID NO 47
<211> LENGTH: 25
<212> TYPE: DNA
```

<213> ORGANISM: Human papillomavirus

<400> SEQUENCE: 47
gggaatccat atgctgtatg tgata                                          25

<210> SEQ ID NO 48
<211> LENGTH: 25
<212> TYPE: DNA
<213> ORGANISM: Human papillomavirus

<400> SEQUENCE: 48
gcaatacaac aaaccgttgt gtgat                                          25

<210> SEQ ID NO 49
<211> LENGTH: 25
<212> TYPE: DNA
<213> ORGANISM: Human papillomavirus

<400> SEQUENCE: 49
cggtggaccg gtcgatgtat gtctt                                          25

<210> SEQ ID NO 50
<211> LENGTH: 25
<212> TYPE: DNA
<213> ORGANISM: Human papillomavirus

<400> SEQUENCE: 50
cgatgtatgt cttgttgcag atcat                                          25

<210> SEQ ID NO 51
<211> LENGTH: 25
<212> TYPE: DNA
<213> ORGANISM: Human papillomavirus

<400> SEQUENCE: 51
gggtacggga tgtaatggat ggttt                                          25

<210> SEQ ID NO 52
<211> LENGTH: 25
<212> TYPE: DNA
<213> ORGANISM: Human papillomavirus

<400> SEQUENCE: 52
cgggtatggc aatactgaag tggaa                                          25

<210> SEQ ID NO 53
<211> LENGTH: 25
<212> TYPE: DNA
<213> ORGANISM: Human papillomavirus

<400> SEQUENCE: 53
gctgcatttg gacttacacc cagta                                          25

<210> SEQ ID NO 54
<211> LENGTH: 25
<212> TYPE: DNA
<213> ORGANISM: Human papillomavirus

<400> SEQUENCE: 54
ggagacacgc cagaatggat acaaa                                          25

<210> SEQ ID NO 55
<211> LENGTH: 25

<212> TYPE: DNA
<213> ORGANISM: Human papillomavirus

<400> SEQUENCE: 55
ggattgtgca acaatgtgta gacat                                  25

<210> SEQ ID NO 56
<211> LENGTH: 25
<212> TYPE: DNA
<213> ORGANISM: Human papillomavirus

<400> SEQUENCE: 56
ggtgcagcta acacaggtaa atcat                                  25

<210> SEQ ID NO 57
<211> LENGTH: 25
<212> TYPE: DNA
<213> ORGANISM: Human papillomavirus

<400> SEQUENCE: 57
ggatgtaaag catagaccat tggta                                  25

<210> SEQ ID NO 58
<211> LENGTH: 25
<212> TYPE: DNA
<213> ORGANISM: Human papillomavirus

<400> SEQUENCE: 58
cgatggagac tctttgccaa cgttt                                  25

<210> SEQ ID NO 59
<211> LENGTH: 25
<212> TYPE: DNA
<213> ORGANISM: Human papillomavirus

<400> SEQUENCE: 59
ggagactctt tgccaacgtt taaat                                  25

<210> SEQ ID NO 60
<211> LENGTH: 25
<212> TYPE: DNA
<213> ORGANISM: Human papillomavirus

<400> SEQUENCE: 60
gctatttatt acaaggccag agaaa                                  25

<210> SEQ ID NO 61
<211> LENGTH: 25
<212> TYPE: DNA
<213> ORGANISM: Human papillomavirus

<400> SEQUENCE: 61
ggaagtgcag tttgatggag acata                                  25

<210> SEQ ID NO 62
<211> LENGTH: 25
<212> TYPE: DNA
<213> ORGANISM: Human papillomavirus

<400> SEQUENCE: 62
gggtcaagtt gactattatg gttta                                  25

<210> SEQ ID NO 63

```
<211> LENGTH: 25
<212> TYPE: DNA
<213> ORGANISM: Human papillomavirus

<400> SEQUENCE: 63
ggaagttcat gcgggtggtc aggta                                    25

<210> SEQ ID NO 64
<211> LENGTH: 25
<212> TYPE: DNA
<213> ORGANISM: Human papillomavirus

<400> SEQUENCE: 64
cgacccatac caaagccgtc gcctt                                    25

<210> SEQ ID NO 65
<211> LENGTH: 25
<212> TYPE: DNA
<213> ORGANISM: Human papillomavirus

<400> SEQUENCE: 65
ccaagatcag agccagacac cggaa                                    25

<210> SEQ ID NO 66
<211> LENGTH: 25
<212> TYPE: DNA
<213> ORGANISM: Human papillomavirus

<400> SEQUENCE: 66
ggcattggac aggacataat gtaaa                                    25

<210> SEQ ID NO 67
<211> LENGTH: 25
<212> TYPE: DNA
<213> ORGANISM: Human papillomavirus

<400> SEQUENCE: 67
gcaacgaagt atcctctcct gaaat                                    25

<210> SEQ ID NO 68
<211> LENGTH: 25
<212> TYPE: DNA
<213> ORGANISM: Human papillomavirus

<400> SEQUENCE: 68
cgaagtatcc tctcctgaaa ttatt                                    25

<210> SEQ ID NO 69
<211> LENGTH: 25
<212> TYPE: DNA
<213> ORGANISM: Human papillomavirus

<400> SEQUENCE: 69
gccgtcgcct tgggcaccga agaaa                                    25

<210> SEQ ID NO 70
<211> LENGTH: 25
<212> TYPE: DNA
<213> ORGANISM: Human papillomavirus

<400> SEQUENCE: 70
ggcaccgaag aaacacagac gacta                                    25
```

```
<210> SEQ ID NO 71
<211> LENGTH: 25
<212> TYPE: DNA
<213> ORGANISM: Human papillomavirus

<400> SEQUENCE: 71
gcaccgaaga aacacagacg actat                                              25

<210> SEQ ID NO 72
<211> LENGTH: 25
<212> TYPE: DNA
<213> ORGANISM: Human papillomavirus

<400> SEQUENCE: 72
cgtgcatcgg ctacccaact ttata                                              25

<210> SEQ ID NO 73
<211> LENGTH: 25
<212> TYPE: DNA
<213> ORGANISM: Human papillomavirus

<400> SEQUENCE: 73
gggtacaggc ggacgcactg ggtat                                              25

<210> SEQ ID NO 74
<211> LENGTH: 25
<212> TYPE: DNA
<213> ORGANISM: Human papillomavirus

<400> SEQUENCE: 74
cccagatgta tcaggattta gtatt                                              25

<210> SEQ ID NO 75
<211> LENGTH: 25
<212> TYPE: DNA
<213> ORGANISM: Human papillomavirus

<400> SEQUENCE: 75
cgcccagtgg cacgcctagg attat                                              25

<210> SEQ ID NO 76
<211> LENGTH: 25
<212> TYPE: DNA
<213> ORGANISM: Human papillomavirus

<400> SEQUENCE: 76
ccactcccac taaacttatt acata                                              25

<210> SEQ ID NO 77
<211> LENGTH: 25
<212> TYPE: DNA
<213> ORGANISM: Human papillomavirus

<400> SEQUENCE: 77
gcagcctcac ctacttctat taata                                              25

<210> SEQ ID NO 78
<211> LENGTH: 25
<212> TYPE: DNA
<213> ORGANISM: Human papillomavirus

<400> SEQUENCE: 78
ccagggtctc cacaatatac aatta                                              25
```

```
<210> SEQ ID NO 79
<211> LENGTH: 25
<212> TYPE: DNA
<213> ORGANISM: Human papillomavirus

<400> SEQUENCE: 79
ggctgcctag tgaggccact gtcta                                    25

<210> SEQ ID NO 80
<211> LENGTH: 25
<212> TYPE: DNA
<213> ORGANISM: Human papillomavirus

<400> SEQUENCE: 80
gctggtttgg gcctgtgtag gtgtt                                    25

<210> SEQ ID NO 81
<211> LENGTH: 25
<212> TYPE: DNA
<213> ORGANISM: Human papillomavirus

<400> SEQUENCE: 81
gcagcaaatg caggtgtgga taata                                    25

<210> SEQ ID NO 82
<211> LENGTH: 25
<212> TYPE: DNA
<213> ORGANISM: Human papillomavirus

<400> SEQUENCE: 82
cccatgtacc aatgttgcag taaat                                    25

<210> SEQ ID NO 83
<211> LENGTH: 25
<212> TYPE: DNA
<213> ORGANISM: Human papillomavirus

<400> SEQUENCE: 83
gggtctactg caaatttagc cagtt                                    25

<210> SEQ ID NO 84
<211> LENGTH: 25
<212> TYPE: DNA
<213> ORGANISM: Human papillomavirus

<400> SEQUENCE: 84
ggaggcacac tagaagatac ttata                                    25

<210> SEQ ID NO 85
<211> LENGTH: 25
<212> TYPE: DNA
<213> ORGANISM: Human papillomavirus

<400> SEQUENCE: 85
cctcatctac ctctacaact gctaa                                    25

<210> SEQ ID NO 86
<211> LENGTH: 25
<212> TYPE: DNA
<213> ORGANISM: Human papillomavirus

<400> SEQUENCE: 86
gcaagacata gaaataacct gtgta                                    25
```

<210> SEQ ID NO 87
<211> LENGTH: 25
<212> TYPE: DNA
<213> ORGANISM: Human papillomavirus

<400> SEQUENCE: 87
cctgtgtata ttgcaagaca gtatt					25

<210> SEQ ID NO 88
<211> LENGTH: 25
<212> TYPE: DNA
<213> ORGANISM: Human papillomavirus

<400> SEQUENCE: 88
cccatgctgc atgccataaa tgtat					25

<210> SEQ ID NO 89
<211> LENGTH: 25
<212> TYPE: DNA
<213> ORGANISM: Human papillomavirus

<400> SEQUENCE: 89
ggtgcctgcg gtgccagaaa ccgtt					25

<210> SEQ ID NO 90
<211> LENGTH: 25
<212> TYPE: DNA
<213> ORGANISM: Human papillomavirus

<400> SEQUENCE: 90
ccagaaaccg ttgaatccag cagaa					25

<210> SEQ ID NO 91
<211> LENGTH: 25
<212> TYPE: DNA
<213> ORGANISM: Human papillomavirus

<400> SEQUENCE: 91
gggcactata gaggccagtg ccatt					25

<210> SEQ ID NO 92
<211> LENGTH: 25
<212> TYPE: DNA
<213> ORGANISM: Human papillomavirus

<400> SEQUENCE: 92
ccgagcacga caggaacgac tccaa					25

<210> SEQ ID NO 93
<211> LENGTH: 25
<212> TYPE: DNA
<213> ORGANISM: Human papillomavirus

<400> SEQUENCE: 93
ggaacgactc caacgacgca gagaa					25

<210> SEQ ID NO 94
<211> LENGTH: 25
<212> TYPE: DNA
<213> ORGANISM: Human papillomavirus

<400> SEQUENCE: 94

```
gcatggacct aaggcaacat tgcaa                                          25

<210> SEQ ID NO 95
<211> LENGTH: 25
<212> TYPE: DNA
<213> ORGANISM: Human papillomavirus

<400> SEQUENCE: 95
ggttgacctt ctatgtcacg agcaa                                          25

<210> SEQ ID NO 96
<211> LENGTH: 25
<212> TYPE: DNA
<213> ORGANISM: Human papillomavirus

<400> SEQUENCE: 96
gcaattaagc gactcagagg aagaa                                          25

<210> SEQ ID NO 97
<211> LENGTH: 25
<212> TYPE: DNA
<213> ORGANISM: Human papillomavirus

<400> SEQUENCE: 97
cgagccgaac cacaacgtca cacaa                                          25

<210> SEQ ID NO 98
<211> LENGTH: 25
<212> TYPE: DNA
<213> ORGANISM: Human papillomavirus

<400> SEQUENCE: 98
gccagaattg agctagtagt agaaa                                          25

<210> SEQ ID NO 99
<211> LENGTH: 25
<212> TYPE: DNA
<213> ORGANISM: Human papillomavirus

<400> SEQUENCE: 99
gctcagcaga cgaccttcga gcatt                                          25

<210> SEQ ID NO 100
<211> LENGTH: 25
<212> TYPE: DNA
<213> ORGANISM: Human papillomavirus

<400> SEQUENCE: 100
gctgtttctg aacaccctgt ccttt                                          25

<210> SEQ ID NO 101
<211> LENGTH: 25
<212> TYPE: DNA
<213> ORGANISM: Human papillomavirus

<400> SEQUENCE: 101
gggcacgggt tgtaacggct ggttt                                          25

<210> SEQ ID NO 102
<211> LENGTH: 25
<212> TYPE: DNA
<213> ORGANISM: Human papillomavirus

<400> SEQUENCE: 102
```

```
ggcaatgtat gtagtggcgg cagta                                          25

<210> SEQ ID NO 103
<211> LENGTH: 25
<212> TYPE: DNA
<213> ORGANISM: Human papillomavirus

<400> SEQUENCE: 103
gggttacagc tatatttgga gtaaa                                          25

<210> SEQ ID NO 104
<211> LENGTH: 25
<212> TYPE: DNA
<213> ORGANISM: Human papillomavirus

<400> SEQUENCE: 104
gctatatttg gagtaaaccc aacaa                                          25

<210> SEQ ID NO 105
<211> LENGTH: 25
<212> TYPE: DNA
<213> ORGANISM: Human papillomavirus

<400> SEQUENCE: 105
ccttattagc agacagcaac agcaa                                          25

<210> SEQ ID NO 106
<211> LENGTH: 25
<212> TYPE: DNA
<213> ORGANISM: Human papillomavirus

<400> SEQUENCE: 106
cgtgttggac atactttgat accta                                          25

<210> SEQ ID NO 107
<211> LENGTH: 25
<212> TYPE: DNA
<213> ORGANISM: Human papillomavirus

<400> SEQUENCE: 107
ggaagaggaa gatgcagaca ccgaa                                          25

<210> SEQ ID NO 108
<211> LENGTH: 25
<212> TYPE: DNA
<213> ORGANISM: Human papillomavirus

<400> SEQUENCE: 108
cgaaggaaac cctttcggaa cgttt                                          25

<210> SEQ ID NO 109
<211> LENGTH: 25
<212> TYPE: DNA
<213> ORGANISM: Human papillomavirus

<400> SEQUENCE: 109
gcaagggaac atggcataca gacat                                          25

<210> SEQ ID NO 110
<211> LENGTH: 25
<212> TYPE: DNA
<213> ORGANISM: Human papillomavirus
```

```
<400> SEQUENCE: 110
ggaatacaga acctactcac tgctt                                            25

<210> SEQ ID NO 111
<211> LENGTH: 25
<212> TYPE: DNA
<213> ORGANISM: Human papillomavirus

<400> SEQUENCE: 111
ggacagtgtg tattatatga ctgat                                            25

<210> SEQ ID NO 112
<211> LENGTH: 25
<212> TYPE: DNA
<213> ORGANISM: Human papillomavirus

<400> SEQUENCE: 112
cggtatccgc tactcagctt gttaa                                            25

<210> SEQ ID NO 113
<211> LENGTH: 25
<212> TYPE: DNA
<213> ORGANISM: Human papillomavirus

<400> SEQUENCE: 113
gcattgtgga cctgtcaacc cactt                                            25

<210> SEQ ID NO 114
<211> LENGTH: 25
<212> TYPE: DNA
<213> ORGANISM: Human papillomavirus

<400> SEQUENCE: 114
ggtaacacta cgcctataat acatt                                            25

<210> SEQ ID NO 115
<211> LENGTH: 25
<212> TYPE: DNA
<213> ORGANISM: Human papillomavirus

<400> SEQUENCE: 115
ggaatactga ctgtaacata ccata                                            25

<210> SEQ ID NO 116
<211> LENGTH: 25
<212> TYPE: DNA
<213> ORGANISM: Human papillomavirus

<400> SEQUENCE: 116
cgacacggta tccgctactc agctt                                            25

<210> SEQ ID NO 117
<211> LENGTH: 25
<212> TYPE: DNA
<213> ORGANISM: Human papillomavirus

<400> SEQUENCE: 117
ggtatccgct actcagcttg ttaaa                                            25

<210> SEQ ID NO 118
<211> LENGTH: 25
<212> TYPE: DNA
<213> ORGANISM: Human papillomavirus
```

```
<400> SEQUENCE: 118
cgctactcag cttgttaaac agcta                                          25

<210> SEQ ID NO 119
<211> LENGTH: 25
<212> TYPE: DNA
<213> ORGANISM: Human papillomavirus

<400> SEQUENCE: 119
ccacttctcg gtgcagctac accta                                          25

<210> SEQ ID NO 120
<211> LENGTH: 25
<212> TYPE: DNA
<213> ORGANISM: Human papillomavirus

<400> SEQUENCE: 120
cggaaactct gtagtggtaa cacta                                          25

<210> SEQ ID NO 121
<211> LENGTH: 25
<212> TYPE: DNA
<213> ORGANISM: Human papillomavirus

<400> SEQUENCE: 121
gccatctgtc tgtatgtgtg cgtat                                          25

<210> SEQ ID NO 122
<211> LENGTH: 25
<212> TYPE: DNA
<213> ORGANISM: Human papillomavirus

<400> SEQUENCE: 122
gcatgggtat tggtatttgt gtata                                          25

<210> SEQ ID NO 123
<211> LENGTH: 25
<212> TYPE: DNA
<213> ORGANISM: Human papillomavirus

<400> SEQUENCE: 123
ccctgccaca gcattcacag tatat                                          25

<210> SEQ ID NO 124
<211> LENGTH: 25
<212> TYPE: DNA
<213> ORGANISM: Human papillomavirus

<400> SEQUENCE: 124
gccacagcat tcacagtata tgtat                                          25

<210> SEQ ID NO 125
<211> LENGTH: 25
<212> TYPE: DNA
<213> ORGANISM: Human papillomavirus

<400> SEQUENCE: 125
ccacagcatt cacagtatat gtatt                                          25

<210> SEQ ID NO 126
<211> LENGTH: 25
<212> TYPE: DNA
```

<210> SEQ ID NO 126
<211> LENGTH: 25
<212> TYPE: DNA
<213> ORGANISM: Human papillomavirus

<400> SEQUENCE: 126
gcccatgtta ctattgcata tacat                                  25

<210> SEQ ID NO 127
<211> LENGTH: 25
<212> TYPE: DNA
<213> ORGANISM: Human papillomavirus

<400> SEQUENCE: 127
gcaaacgggc ttcggtaact gactt                                  25

<210> SEQ ID NO 128
<211> LENGTH: 25
<212> TYPE: DNA
<213> ORGANISM: Human papillomavirus

<400> SEQUENCE: 128
gggtacattc cattgggtgg gcgtt                                  25

<210> SEQ ID NO 129
<211> LENGTH: 25
<212> TYPE: DNA
<213> ORGANISM: Human papillomavirus

<400> SEQUENCE: 129
gggtttgata taacatctgc gggta                                  25

<210> SEQ ID NO 130
<211> LENGTH: 25
<212> TYPE: DNA
<213> ORGANISM: Human papillomavirus

<400> SEQUENCE: 130
ccctacatct ggaacacatg ggtat                                  25

<210> SEQ ID NO 131
<211> LENGTH: 25
<212> TYPE: DNA
<213> ORGANISM: Human papillomavirus

<400> SEQUENCE: 131
cctaccaaca agtgtcagtg gctaa                                  25

<210> SEQ ID NO 132
<211> LENGTH: 25
<212> TYPE: DNA
<213> ORGANISM: Human papillomavirus

<400> SEQUENCE: 132
gcaactatgt ttacccgcag cggta                                  25

<210> SEQ ID NO 133
<211> LENGTH: 25
<212> TYPE: DNA
<213> ORGANISM: Human papillomavirus

<400> SEQUENCE: 133
cggaggacaa tgacttgttt gatat                                  25

<210> SEQ ID NO 134
<211> LENGTH: 25

<212> TYPE: DNA
<213> ORGANISM: Human papillomavirus

<400> SEQUENCE: 134
cctcctcttg ggatgtgcct gtata                                              25

<210> SEQ ID NO 135
<211> LENGTH: 25
<212> TYPE: DNA
<213> ORGANISM: Human papillomavirus

<400> SEQUENCE: 135
cctgcctcta cacagtatat tggta                                              25

<210> SEQ ID NO 136
<211> LENGTH: 25
<212> TYPE: DNA
<213> ORGANISM: Human papillomavirus

<400> SEQUENCE: 136
gggtgcagtt acctgaccca aataa                                              25

<210> SEQ ID NO 137
<211> LENGTH: 25
<212> TYPE: DNA
<213> ORGANISM: Human papillomavirus

<400> SEQUENCE: 137
ggatatggtg ccatggactt tagta                                              25

<210> SEQ ID NO 138
<211> LENGTH: 25
<212> TYPE: DNA
<213> ORGANISM: Human papillomavirus

<400> SEQUENCE: 138
cctctgactc ccagttgttt aataa                                              25

<210> SEQ ID NO 139
<211> LENGTH: 25
<212> TYPE: DNA
<213> ORGANISM: Human papillomavirus

<400> SEQUENCE: 139
ggtagatacc actcccagta ccaat                                              25

<210> SEQ ID NO 140
<211> LENGTH: 25
<212> TYPE: DNA
<213> ORGANISM: Human papillomavirus

<400> SEQUENCE: 140
ccactcccag taccaattta acaat                                              25

<210> SEQ ID NO 141
<211> LENGTH: 25
<212> TYPE: DNA
<213> ORGANISM: Human papillomavirus

<400> SEQUENCE: 141
ccaactacta gtttggtgga tacat                                              25

<210> SEQ ID NO 142

```
<210> SEQ ID NO 142
<211> LENGTH: 25
<212> TYPE: DNA
<213> ORGANISM: Human papillomavirus

<400> SEQUENCE: 142
ccactacgtc ttctaaacct gccaa                                              25

<210> SEQ ID NO 143
<211> LENGTH: 25
<212> TYPE: DNA
<213> ORGANISM: Human papillomavirus

<400> SEQUENCE: 143
cctgttgctg tggatgtgac agcaa                                              25

<210> SEQ ID NO 144
<211> LENGTH: 25
<212> TYPE: DNA
<213> ORGANISM: Human papillomavirus

<400> SEQUENCE: 144
ggacagtgga tatggctatt ctgaa                                              25

<210> SEQ ID NO 145
<211> LENGTH: 25
<212> TYPE: DNA
<213> ORGANISM: Human papillomavirus

<400> SEQUENCE: 145
cgaggaagat ggaagcaata gccaa                                              25

<210> SEQ ID NO 146
<211> LENGTH: 25
<212> TYPE: DNA
<213> ORGANISM: Human papillomavirus

<400> SEQUENCE: 146
ggaagcaata gccaagcgtt tagat                                              25

<210> SEQ ID NO 147
<211> LENGTH: 25
<212> TYPE: DNA
<213> ORGANISM: Human papillomavirus

<400> SEQUENCE: 147
ggaagtatgt tatggcagca cagtt                                              25

<210> SEQ ID NO 148
<211> LENGTH: 25
<212> TYPE: DNA
<213> ORGANISM: Human papillomavirus

<400> SEQUENCE: 148 cccttagtc ctgtaactcc tgctt                                               25

<210> SEQ ID NO 149
<211> LENGTH: 25
<212> TYPE: DNA
<213> ORGANISM: Human papillomavirus

<400> SEQUENCE: 149
cctttagtcc tgtaactcct gcttt                                              25
```

```
<210> SEQ ID NO 150
<211> LENGTH: 25
<212> TYPE: DNA
<213> ORGANISM: Human papillomavirus

<400> SEQUENCE: 150
cctgctttac ctacaggccc tgttt                                    25

<210> SEQ ID NO 151
<211> LENGTH: 25
<212> TYPE: DNA
<213> ORGANISM: Human papillomavirus

<400> SEQUENCE: 151
ggcggcctag cgacagcaca gtata                                    25

<210> SEQ ID NO 152
<211> LENGTH: 25
<212> TYPE: DNA
<213> ORGANISM: Human papillomavirus

<400> SEQUENCE: 152
gcggcctagc gacagcacag tatat                                    25

<210> SEQ ID NO 153
<211> LENGTH: 25
<212> TYPE: RNA
<213> ORGANISM: Human papillomavirus

<400> SEQUENCE: 153
gcaugaauau auguuagauu ugcaa                                    25

<210> SEQ ID NO 154
<211> LENGTH: 25
<212> TYPE: RNA
<213> ORGANISM: Human papillomavirus

<400> SEQUENCE: 154
ggacagagcc cauuacaaua uugua                                    25

<210> SEQ ID NO 155
<211> LENGTH: 25
<212> TYPE: RNA
<213> ORGANISM: Human papillomavirus

<400> SEQUENCE: 155
gcccauuaca auaccguaac cuuuu                                    25

<210> SEQ ID NO 156
<211> LENGTH: 25
<212> TYPE: RNA
<213> ORGANISM: Human papillomavirus

<400> SEQUENCE: 156
ggaagaccug uuaaugggca cacua                                    25

<210> SEQ ID NO 157
<211> LENGTH: 25
<212> TYPE: RNA
<213> ORGANISM: Human papillomavirus

<400> SEQUENCE: 157
ccuguuaaug ggcacacuag gaauu                                    25
```

```
<210> SEQ ID NO 158
<211> LENGTH: 25
<212> TYPE: RNA
<213> ORGANISM: Human papillomavirus

<400> SEQUENCE: 158
gcacacuagg aauugugugc cccau                                              25

<210> SEQ ID NO 159
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gcatgaatat atgttggatc tgca                                               24

<210> SEQ ID NO 160
<211> LENGTH: 70
<212> TYPE: DNA
<213> ORGANISM: Human papillomavirus

<400> SEQUENCE: 160
atgcatggag atacacctac attgcatgaa tatatgttag atttgcaacc agagacaact        60
gatctctact                                                               70

<210> SEQ ID NO 161
<211> LENGTH: 25
<212> TYPE: DNA
<213> ORGANISM: Human papillomavirus

<400> SEQUENCE: 161
gcatgaatat atgttagatt tgcaa                                              25

<210> SEQ ID NO 162
<211> LENGTH: 70
<212> TYPE: DNA
<213> ORGANISM: Human papillomavirus

<400> SEQUENCE: 162
gttatgagca attaaatgac agctcagagg aggaggatga aatagatggt ccagctggac        60
aagcagaacc                                                               70

<210> SEQ ID NO 163
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gcccactaca acatcgtgac ctttt                                              25

<210> SEQ ID NO 164
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 164
ggacagagcc cactacaaca tcgt                                        24

<210> SEQ ID NO 165
<211> LENGTH: 83
<212> TYPE: DNA
<213> ORGANISM: Human papillomavirus

<400> SEQUENCE: 165
ggacagagcc cattacaata ttgtaacctt tgttgcaag tgtgactcta cgcttcggtt    60
gtgcgtacaa agcacacacg tag                                         83

<210> SEQ ID NO 166
<211> LENGTH: 25
<212> TYPE: DNA
<213> ORGANISM: Human papillomavirus

<400> SEQUENCE: 166
gcccattaca atattgtaac ctttt                                       25

<210> SEQ ID NO 167
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 167
gcaccctggg catcctgtgc cccat                                       25

<210> SEQ ID NO 168
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 168
cctgctgatg ggcaccctgg gcat                                        24

<210> SEQ ID NO 169
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 169
ggaagacctg ctgatgggca ccct                                        24

<210> SEQ ID NO 170
<211> LENGTH: 74
<212> TYPE: DNA
<213> ORGANISM: Human papillomavirus

<400> SEQUENCE: 170
acattcgtac tttggaagac ctgttaatgg gcacactagg aattgtgtgc cccatctgtt    60
ctcagaaacc ataa                                                   74

<210> SEQ ID NO 171

```
<211> LENGTH: 25
<212> TYPE: DNA
<213> ORGANISM: Human papillomavirus

<400> SEQUENCE: 171
gcacactagg aattgtgtgc cccat                                             25
```

SIRNA COMPOSITIONS AND METHODS FOR TREATMENT OF HPV AND OTHER INFECTIONS

CROSS-REFERENCE TO RELATED PATENT APPLICATIONS

This application is a continuation-in-part of, and claims the benefit under 35 U.S.C. §§120 and 365(c) of, International Patent Application No. PCT/US2011/045884, filed Jul. 29, 2011, which claims priority to, and the benefit of, U.S. Provisional Patent Application No. 61/369,067, filed Jul. 29, 2010, the contents of each of which are expressly incorporated by reference herein in their entirety.

SEQUENCE LISTING

The instant application contains a Sequence Listing which has been submitted in ASCII format via EFS-Web and is hereby incorporated by reference in its entirety. Said ASCII copy, created on Sep. 4, 2013, is named SIR-009-P001-US_SL.txt and is 29,728 bytes in size.

FIELD OF INVENTION

The invention relates to siRNA molecules, compositions, and methods for the treatment of human papillomavirus (HPV) infections and certain other infections, in particular, HIV, HSV, and fungal infections. The compositions include a cocktail of siRNA molecules targeted against HPV, formulated with dendrimer, a polymer which is effective against HIV and HSV infections. The compositions also include a cocktail of siRNA molecules targeted against HPV, formulated with histidine-lysine (HK) polymer, a polymer which has been shown to be effective in vitro to inhibit fungal infections.

BACKGROUND

HPV and Cervical Cancer

Human Papilloma Virus (HPV) is a group of coated DNA viruses, which now has over 100 different species, and is the most common sexually transmitted (ST) infection in adults worldwide. In 1976 Harald zur Hausen from Germany published the hypothesis that human Papilloma virus plays an important role in the cause of cervical cancer tissue [1]. In 1983 and 1984 zur Hausen and his collaborators identified HPV16 and HPV18 in cervical cancer [2-4]. Dr. zur Hausen was awarded the Nobel Prize for Physiology and Medicine in 2008, because of his contribution. It is estimated that over 80% of US women by age 50 will have contracted at least one strain of HPV [5]. It is also estimated that each year there are 490,000 new cases of cervical cancer worldwide, which result in 270,000 deaths. In the US, each year there are 250,000 to 1 million women who develop cervical dysplasia, which leads to 11,000 further developing cervical cancer, and to 4,000 deaths [6]. Among the 19 "high-risk" HPVs which will lead to cervical cancer, HPV16 and 18 count for about 70% of the cases [7].

HPVs have a circular genome of about 8 kb, with three major regions in the genome, the early genes (E6, E7, E1, E2, E4 and E5), the late genes (L1 and L2), and the long control region (LCR) between L1 and E6. FIG. 1 shows the characteristic HPV genome organization, using the medically important HPV-18 as the model. The early transcripts ending at 4215 encode the 6 early genes, while the late transcripts ending at 7221 encode the two late genes. E6 and E7 are cancer transforming proteins because they inactivate tumor suppressor proteins p53 (inactivated by E6) and pRb (inactivated by E7) [8].

Although the US FDA has approved two HPV vaccines (below), there is still a high demand for HPV therapeutics. However, there is no effective treatment on the market yet [9]. This invention describes HPV therapeutics by siRNAs complexed with dendrimer and histidine-lysine polymers.

HPV Vaccine

In 2006, the US FDA approved Gardasil®, an HPV vaccine produced by Merck, which is composed of hollow virus-like particles (VLP) assembled from recombinant HPV coat proteins and which targets HPV16, 18, 6 and 11. The vaccine is aimed at use in women and girls. Later, it was reported that Gardasil® is also effective in preventing genital warts in males. The use of Gardasil® for men and boys was approved by the FDA on Oct. 16, 2009. In October 2009, the FDA also approved Cervarix®, the second HPV vaccine targeting HPV16 and 18 and produced by GlaxoSmithKline [10].

Public health officials in industrialized counties and areas like Australia, Canada, Europe and the US recommend vaccination of young women against HPV to prevent cervical cancer and genital warts, and to reduce the number of painful and costly treatments for cervical dysplasia caused by HPV infections. It is recommended that women and girls who are not exposed to HPVs between the ages of 9 to 25 should get an HPV vaccination [11]. However, many women and girls are not vaccinated because of various reasons. In the US, only about one-quarter of girls got HPV vaccination because most families worried about either the effectiveness or the side effects of the vaccine [12]. In addition, HPV vaccines are not very easy to get access to in third world countries. In Kenya as an example, the cost of vaccination is over the average annual income of a family [13]. Furthermore, many women have been exposed to HPVs already [14].

Dendrimer and Clinical Trials for HIV and HSV Treatment and HPV Inhibition In Vitro Dendrimers are dendritic polymers which belong to a new class of polymer architecture (after traditional linear, cross-linked and branched types) [15]. VivaGel® (SPL7013), an anionic poly (L-Lysine) dendrimer, has been applied in at least 4 different clinical trials [16]. A phase I trial, completed on Jan. 20, 2008, tested male tolerance for topical application of SPL7013. Phase I and II trials, completed on Jun. 4, 2009, of vaginal dosing tested against HIV infection and HSV-2 herpes in women. A phase I trial, completed on Feb. 2, 2010, tested acceptability of SPL7013 in sexually active women. A phase I trial, completed on Mar. 4, 2010, was a safety test for HSV-2 infection in health young women. Australian and US NCI laboratories also showed that SPL7013 inhibits clinically relevant strains of HPV in vitro [17].

HK Polymers Inhibit Fungal Infections In Vitro

It was shown that histidine-lysine polymers are able to inhibit the growth of fungal strains, C. albicans and C. kefyr [18]. The highest inhibition activity was achieved by HK polymer H2K4b (MW, 11,137). The structure of H2K4b is as follows: KKK(KHKHHKHHKHHKHHKHHKHK)4 (core sequence disclosed as SEQ ID NO: 1)

RNAi and Development of Novel Therapeutics

RNA interference (RNAi) was first illustrated in plants, but quickly proved to be a universal process covering low and high biological species. It is an efficient process in which double-stranded RNA duplexes were generated and lead to sequence specific target RNA recognition, binding and degradation [19]. In recent years RNAi was not only applied in various biological studies, but applied in therapeutic development as well [20]. To date, at least 15 therapeutic programs developed from RNAi are in different stages of or have finished clinical trials [21].

Delivery Vehicles for siRNA Therapeutics

Even though siRNAs provide a very attractive technology to be developed into innovative therapeutics, many of the programs didn't succeed. Failed siRNA therapeutic programs either in preclinical studies or in clinical trials have proved that siRNA molecules designed to target various genes could not apply to animals or human beings directly because of stability issues [20]. Naked siRNAs have to be modified to protect them from degradation, or to be packed with other molecules either to facilitate cell entry or to be functional to decrease target gene expression [22]. Therefore, the development of delivery methods has been one of the most important areas in the research and development of siRNA therapeutics [23].

BRIEF DESCRIPTION OF THE FIGURES

Figure 1C:
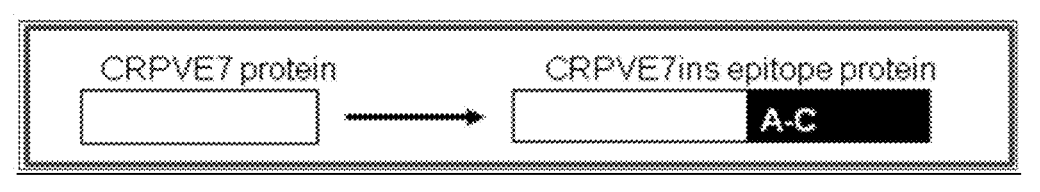

FIG. 1B. SiRNA Designed Targeting Wild-type E7 gene of HPV16 and Hybrid E7 Gene from HPV16 and CRPV. The red blocks are CRPV sequences used to replace the correspondent HPV16 fragments. The yellow highlights in the CRPV E7 siRNAs reflect the codon optimization results. Figure discloses SEQ ID NOS 159-165, 22, 166-170, 27-28, and 171, respectively, in order of appearance.

FIG. 1C. Chimeric human rabbit papilloma virus (cH-RPV) gene construction. The 3 epitope sequences A, B and C (corresponding to the red blocks highlighted in FIGS. 1A and 1B) from HPV16 E7 gene were inserted in the end of CRPV E7 gene in the same reading frame.

FIG. 11. Data summary of the treatment of cH-RPV by different siRNAs. The effective siRNAs are highlighted.

DESCRIPTION OF THE INVENTION

Figure 1A:
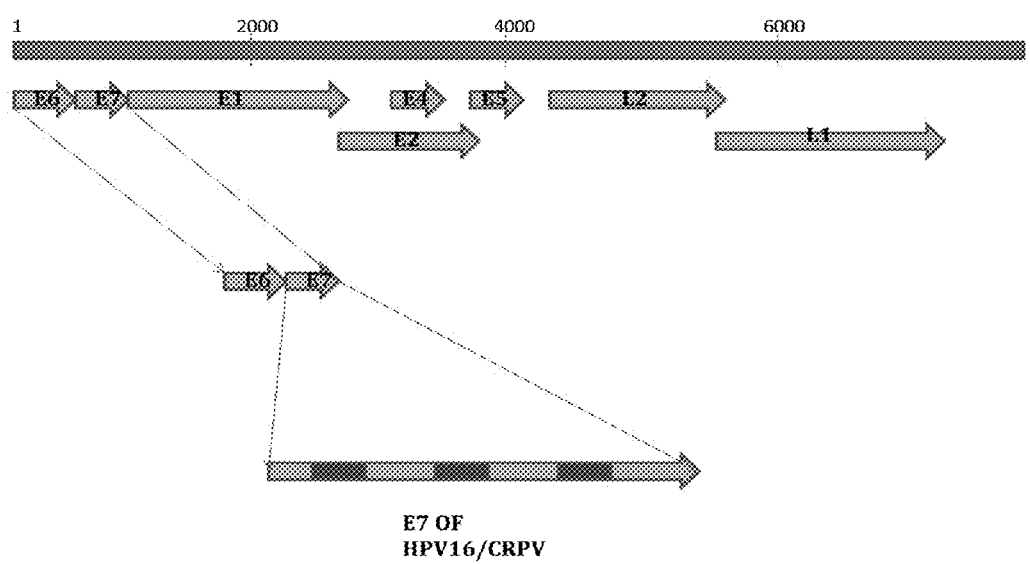
FIG. 1A. HPV Genome and siRNA Designed Targeting Hybrid E7 Gene from HPV16 and Cotton Rabbit Papilloma Virus (CRPV). The E7 gene is enlarged in the bottom and with the three CRPV motifs marked as red blocks.

The invention provides siRNA molecules, compositions containing the molecules, and methods for using the molecules and compositions to treat HPV infections and certain other infections, in particular, HIV, HSV, and fungal infections. The compositions include a cocktail of siRNA molecules targeted against HPV, formulated with dendrimer, a polymer which is effective against HIV and HSV infections. The compositions also include a cocktail of siRNA molecules targeted against HPV, formulated with histidine-lysine (HK) polymer, a polymer which has been shown to be effective in vitro to inhibit fungal infections.

As used herein, an "siRNA molecule" or an "siRNA duplex" is a short, double-stranded oligonucleotide that interferes with the activity of RNA expressed by a gene in a cell, after the molecule is introduced into the cell. The molecules are constructed by techniques known to those skilled in the art, given the teachings disclosed herein. Such techniques are described in U.S. Pat. Nos. 5,898,031, 6,107,094, 6,506,559, and 7,056,704 and in European Pat. Nos. 1214945 and 1230375, which are incorporated herein by reference in their entireties.

The siRNA molecule of the invention is an isolated siRNA molecule that binds to a single stranded RNA molecule, which is a messenger RNA (mRNA) that encodes at least part of a peptide or protein of a human papillomavirus (HPV). The mRNA can be encoded by any gene in an HPV, including an early or late stage viral proliferation gene. In one embodiment, the siRNA molecule binds to mRNA molecules from different species of HPV. In one particular embodiment, the HPV species is HPV16, HPV18, HPV6, or HPV11.

In one embodiment, the molecule is an oligonucleotide with a length of about 19 to about 35 base pairs. In another embodiment, the molecule is an oligonucleotide with a length of about 19 to about 27 base pairs. In still another embodiment, the molecule is an oligonucleotide with a length of about 21 to about 25 base pairs. In one particular embodiment, it has 25 base pairs. In all of these embodiments, the molecule may have blunt ends at both ends, or sticky ends at both ends, or a blunt end at one end and a sticky end at the other. In one particular embodiment, it has blunt ends at both ends.

The siRNA molecule can be made of naturally occurring ribonucleotides, i.e., those found in living cells, or one or more of its nucleotides can be chemically modified by techniques known in the art. In addition to being modified at the level of one or more of its individual nucleotides, the backbone of the oligonucleotide also can be modified. Additional modifications include the use of small molecules (e.g. sugar molecules), amino acid molecules, peptides, cholesterol and other large molecules for conjugation onto the siRNA molecules. Such modifications can protect the molecule from degradation, improve its potency, reduce its toxicity, and reduce its immune stimulatory effect.

The siRNA molecule may further comprise an immune stimulatory motif. Such motifs can include specific RNA sequences such as 5'-UGUGU-3' (Judge et al., Nature Biotechnology 23, 457-462 (1 Apr. 2005)), 5'-GUCCUUCAA-3' (Hornung et al., Nat. Med. 11, 263-270(2005). See Kim et al., Mol Cell 24; 247-254 (2007). These articles are incorporated herein by reference in their entireties. These are siRNA sequences that specifically activate immune responses through Toll-like receptor (TLR) activation or through activation of key genes such as RIG-I or PKR. In one embodiment, the motif induces a TH1 pathway immune response. In another embodiment, the motif comprises 5'-UGUGU-3',5'-GUCCUUCAA-3',5'-GGGxGG-3' (where x is A, T, G and C), or CpG motifs 5'-GTCGTT-3'.

Particular target sequences are shown in Tables 1-4 herein. Thus, certain particular siRNA molecules of the invention bind to and inhibit expression of one or more of the sequences identified in these tables. Because the siRNA molecules are duplexes, with one strand being complementary to the target mRNA and the other including the same sequence as the target sequence in the mRNA, the sequences shown in Tables 1-4 also represent certain specific siRNA molecules of the invention.

The siRNA molecules of the invention also include ones derived from those listed in Tables 1-4. The derived molecules can have less than the 25 base pairs shown for each duplex, down to 16 base pairs, so long as the "core" base pairs remain. That is, once given the specific sequences shown in the tables, a person skilled in the art can synthesize molecules that, in effect, "remove" one or more base pairs from either or both ends in any order, leaving the remaining contiguous base pairs, creating shorter molecules that are 24, 23, 22, 21, 20, 19, 18, 17, or 16 base pairs in length. Thus, the derived molecules consist of: a) 24 contiguous base pairs of any one or more of the molecules in Tables 1-4; b) 23 contiguous base pairs of any one or more of the molecules in Tables 1-4; c) 22 contiguous base pairs of any one or more of the molecules in Tables 1-4; b) 21 contiguous base pairs of any one or more of the molecules in Tables 1-4; d) 20 contiguous base pairs of any one or more of the molecules in Tables 1-4; e) 19 contiguous base pairs of any one or more of the molecules in Tables 1-4; f) 18 contiguous base pairs of any one or more of the molecules in Tables 1-4; g) 17 contiguous base pairs of any one or more of the molecules in Tables 1-4; and h) 16 contiguous base pairs of any one or more of the molecules in Tables 1-4. It is not expected that molecules shorter than 16 base pairs would have sufficient activity or sufficiently low off-target effects to be pharmaceutically useful; however, if any such constructs did, they would be equivalents within the scope of this invention.

Alternatively, the derived molecules can have more than the 25 base pairs shown for each duplex, so long as the "core" base pairs remain. That is, once given the specific sequences shown in the tables, a person skilled in the art can synthesize molecules that, in effect, "add" one or more base pairs to either or both ends in any order, creating molecules that are 26 or more base pairs in length and containing the original 25 contiguous base pairs.

In one embodiment, the molecule includes a potency enhancer motif. As used herein, a potency enhancer motif (PEM) is a sequence in the siRNA molecule that increases the therapeutic effect of the molecule in an animal model compared to the same molecule without the sequence. Examples of such motifs are ACTCC and GGAGT.

The invention also includes compositions of one or more of the siRNA molecules. Where there is a plurality of different siRNA molecules, each one targets a different RNA nucleotide sequence, which can be on the same RNA target molecule, different RNA target molecules, or any combination thereof. These compositions, by themselves or in combination with pharmaceutically acceptable carriers such as those described herein, are sometimes called siRNA cocktails. Thus, the invention provides multi-targeted siRNA cocktails for the treatment of HPV.

All possible combinations of types of molecules and targets are included in the invention. For example, the targeted mRNA molecules may encode or regulate the expression of one or more HPV proteins. In one embodiment, the composition comprises two or more different siRNA molecules, each binding to a different mRNA target sequence. In another embodiment, the composition comprises three different siRNA molecules, each binding to a different mRNA target sequence. In still another embodiment, the composition comprises more than three different siRNA molecules, each binding to a different RNA target sequence. In one embodiment, the siRNA molecules target one or more of the mRNA sequences that are transcribed from one or more of the gene sequences listed in Tables 1-4 herein. For example, the cocktail can inhibit expression of one or more of HPV E6, E7, E1, E2, E4, E5, L2, and L1 genes in human tissue. In one embodiment, it inhibits expression of two or more HPV E6, E7, E1, E2, E4, E5, L2, and L1 genes.

As previously mentioned, the siRNA cocktails of the invention comprise two or more different siRNA molecules of the invention in a pharmaceutically acceptable carrier. Such carriers are generally known to those skilled in the art and include saline, sugar solutions, polypeptides, polymers, lipids, creams, gels, micelle materials, and metal nanoparticles.

In one embodiment, the carrier comprises at least one of the following: a glucose solution, a polycationic binding agent, a cationic lipid, a cationic micelle, a cationic polypeptide, a hydrophilic polymer grafted polymer, a non-natural cationic polymer, a cationic polyacetal, a hydrophilic polymer grafted polyacetal, a ligand functionalized cationic polymer, a ligand functionalized-hydrophilic polymer grafted polymer, a ligand functionalized liposome, dendrimer, dendrimer solutions, HK polymer, and HK polymer solutions. Examples of polymers include a biodegradable histidine-lysine polymer, a biodegradable polyester, such as poly(lactic acid) (PLA), poly(glycolic acid) (PGA), and poly(lactic-co-glycolic acid) (PLGA), a polyamidoamine (PAMAM) dendrimer, a cationic lipid, or a PEGylated PEI. Cationic lipids include DOTAP, DOPE, DC-Chol/DOPE, DOTMA, and DOTMA/DOPE. In still another embodiment, the carrier is a histidine-lysine copolymer that forms a nanoparticle with the siRNA molecule, wherein the diameter of the nanoparticle is about 100 nm to about 400 nm.

The invention also provides a nanoparticle comprising one or more of the siRNA molecules of the invention, a pharmaceutically acceptable carrier, such as one or more of those described herein, and a targeting ligand. Examples of such ligands include one or more of an RGD peptide, such as H-ACRGDMFGCA-OH (SEQ ID NO: 2), an RVG peptide, such as H-YTIWMPENPRPGTPCDIFTNSRG-KRASNG-OH (SEQ ID NO: 3), or a FROP peptide, such as H-EDYELMDLLAYL-OH (SEQ ID NO: 4).

The molecules and compositions of the invention interfere with viral replication of HPV. Certain of the compositions also (1) interfere with viral replication of herpes simplex virus (HSV) and human immunodeficiency virus (HIV) in mucosal tissues, such as genital tissues, and (2) treat fungal infections. The molecules and compositions of the invention are used to treat and/or prevent HPV, HSV, HIV, and fungal infections.

The invention also provides a method of treating a mammal with an HPV infection by administering to the mammal a therapeutically effective amount of one or more of the siRNA molecules of the invention or a therapeutically effective amount of one or more of the compositions of the invention. In one embodiment, the mammal is a human, non-human primate, or rodent, such as a mouse, rat, or guinea pig. Rodents are particularly useful for laboratory experiments. In a particular embodiment, the mammal is a human patient.

The compositions are administered by techniques known to those skilled in the art. In one embodiment, the composition comprises at least three siRNA molecules at a ratio determined by the potency of each siRNA molecule and the therapeutic needs of the mammal. In another embodiment, the composition comprises three different siRNA molecules at a ratio of 1:1:1, 1:1.5:0.5, or 0.5:0.5:2.

Certain compositions of the invention have an anti-HIV and an anti-HSV activity, and others have an anti-fungal activity. As mentioned above, dendrimer has an anti-HIV and an anti-HSV activity, and HK polymer has an anti-fungal activity. Therefore, the invention includes a method of treating a mammal with an HPV infection and with an HIV and/or HSV infection comprising administering to the mammal a pharmaceutically effective amount of a composition comprising one or more siRNA molecules of the invention and dendrimer. It further includes a method of treating a mammal with an HPV infection and a fungal infection comprising administering to the mammal a pharmaceutically effective amount of a composition comprising one or more siRNA molecules of the invention and an HK polymer.

The compositions of the invention also can be used with a therapeutically effective amount of other anti-infective agents.

The siRNA molecules and compositions of the invention can also be used prophylactically against HPV, HSV, HIV, and fungal infections. A therapeutically effective amount of one or more of the siRNA molecules of the invention or a therapeutically effective amount of one or more of the compositions of the invention are administered to a mammal. In one embodiment, the mammal is a human patient.

The following examples illustrate certain aspects of the invention and should not be construed as limiting the scope thereof.

EXPERIMENTAL DESIGN, TECHNIQUES, AND EXAMPLES

Prepare Potent siRNA Duplexes Targeted to Genes in HPV16, HPV18, HPV6, and HPV11

In the preliminary studies, we have demonstrated that 25-mer siRNAs are most potent at inhibiting the expression of a specific gene. To ensure the potency of each siRNA molecule for the target gene knockdown, several key features should be considered during the in silico design and the later in vitro and in vivo tests so that the siRNAs:
(1) have the optimum thermodynamics for target sequence binding;
(2) have sufficient length for RISC binding;
(3) have eliminated (or added) immune stimulating motifs;
(4) have minimized "Off-Target" potential;
(5) pass through patent searching with no conflict with the current patents; and
(6) have no interaction when multiple sequences are mixed in a cocktail.

In this invention, we designed siRNA duplexes targeting the conserved gene sequences shared by as many HPV species as possible to increase the universality of the siRNAs. In addition, our preliminary results have demonstrated that 25mer siRNA is more potent than 21mer siRNA. We use 25mer siRNA as our design for the multi-targeted siRNA cocktail targeting to both early (E6, E7, E1, E2, E4, E5) and late (L2 and L1) genes simultaneously (FIG. 1A). All the gene silencing potencies were tested and validated first in the cell culture experiments by RT-PCR and ELISA for efficacy of multi-targeting siRNA on gene knockdown at both transcription and translation levels. Once the most effective siRNA duplexes are selected for both early and late genes from the gene knockdown experiments in cell culture models, we further investigated the optimal combination of siRNA set as the active pharmaceutical ingredient (API) and tested optimized siRNA combinations in a rabbit model.

Applying our siRNA duplexes in cell based high throughput screening, we were able to select the most effective siRNA molecules to reduce HPV16, HPV18, HPV6, and HPV11 gene expression. The siRNAs target all 8 genes of E6, E7, E1, E2, E4, E5, L2 and L1 from HPV16, 18, 6 and 11 with some of the siRNA incorporating the Potency Enhancer Motif (PEM) sequence. (See below.)

Molecular Design of siRNA Sequence

Table 1 shows the siRNAs designed against the 7 genes from HPV16 (with no qualified siRNAs for the E5 gene). Table 2 shows the siRNAs designed against the 8 genes in HPV18. Tables 3 and 4 are the common siRNAs for both HPV6 and HPV11. Generally, we choose 8 siRNAs for each gene. If there are not enough qualified siRNAs, the number will be less than 8. The genes are arranged according to the transcription starting sites. Each gene also marked the transcription start and stop sites. The Potency Enhancer Motif (PEM) sequence (GGAGT) and the reversed strand (ACTCC) are highlighted with yellow or green, respectively.

We have designed 8 siRNAs for each gene in HPV strain (selected from about 400 siRNA pools for each HPV strain). The following are the specific sequences of siRNA targeting each gene for each individual HPV strain. In HPV16, we did not find any qualified siRNA for gene E5 based on the parameters we set for selection in silico in above section. In addition, we found only 7 qualified siRNAs for gene E4. Furthermore, #163 and #167 target both genes of E2 and E4. The overlap has reduced the total number of unique sequences of siRNA for HPV16 to 53 (Table 1).

In HPV18, there are only 7 and 6 siRNA molecules which are qualified for gene E4 and E5, respectively, based on our selection criteria summarized in previous section (Table 2). In addition, #173 and #178 target both genes E2 and E4. Thus, our total number of unique siRNAs for HPV18 is reduced to 59 (Table 2).

In contrast with HPV16 and 18, where we could not find any siRNAs of 25-mer which share the same the common sequence between 16 and 18, in HPV6 and 11, among the siRNAs we have designed (about 250 for each), we have found 10 common siRNAs for both HPV-6 and HPV-11 as shown in Table 3. The 10 common siRNAs target the following genes in both HPV6 and 11: E7, E1, E2, L2 and L1. The common siRNAs found in HPV6 and 11 has made our selection process simpler and easier. We only need to synthesize the 10 siRNAs and test their ability to reduce the expression of HPV6 and 11 genes.

In order to screen potent siRNAs in an in vivo rabbit model [24], we have inserted a codon optimized cotton rabbit papilloma viral (CRPV) gene motif in HPV16 E7, and designed siRNAs to target the CRPV motif and adjacent HPV16 E7 gene (FIGS. 1A and 1B, Table 4). The siRNAs were screened in SiHa cells to choose the ones which can knock down the E7 gene expression.

Potency Enhancer Motif (PEM) Sequence

Table 1 lists the siRNAs designed against the 8 genes from HPV16. Table 2 lists the siRNAs designed against the 8 genes in HPV18. Table 3 and 4 are the common siRNA molecules targeting both HPV6 and HPV11. The genes are arranged according to the transcription starting sites. Each gene also marked the transcription start and stop sites. The Potency Enhancer Motif (PEM) sequence (GGAGT) and reversed strand (ACTCC) are shown.

We chose 8 siRNAs molecules for each of the 8 genes in both HPV16 and HPV18, with some exceptions (see below). In HPV16, we did not find a qualified siRNA for gene E5 based on the parameters we set for selection in silico. We found 7 qualified siRNAs for gene E4. Among the 55 siRNA molecules for HPV16, three of them (#231, #232 and #315) are with Potency Enhancer Motif (PEM) (GGAGU/ACUCC) sequences, and targeting genes L2 and L1, respectively (Table 1). #163 and #167 target both genes of E2 and E4. The overlap has reduced the total number of unique sequence of siRNA to 53.

In HPV18, there are 7 and 6 siRNAs qualified for genes E4 and E5, respectively, based on our selection criteria summarized in previous section (Table 2). In addition, #173 and #178 target both genes E2 and E4. Thus our total number of unique siRNAs for HPV18 is 59 (Table 2). Among the 59 siRNA molecules for HPV 18, 9 of them (#25, $26, #38, #78, #79, #87, #345, #350, and #351) are with Potency Enhancer Motif sequences. Two of the siRNA molecules (#25 and #26) are for E6 gene, one (#38) is for E7 gene, three (#78, #79, and #87) are for E1 gene, and three (#345, #350 and #351) are for L1 gene (Table 2).

Figure 2:
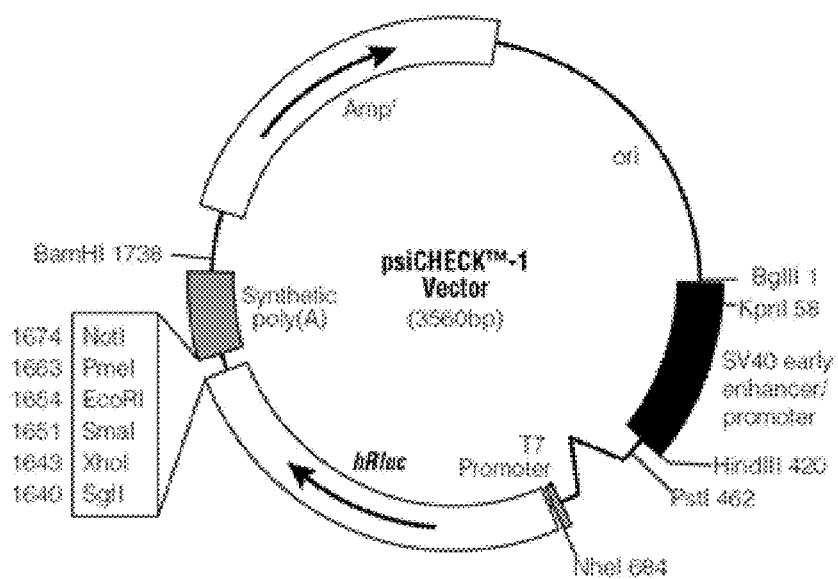
FIG. 2. psiCHECK-1 map.
Figure 3:
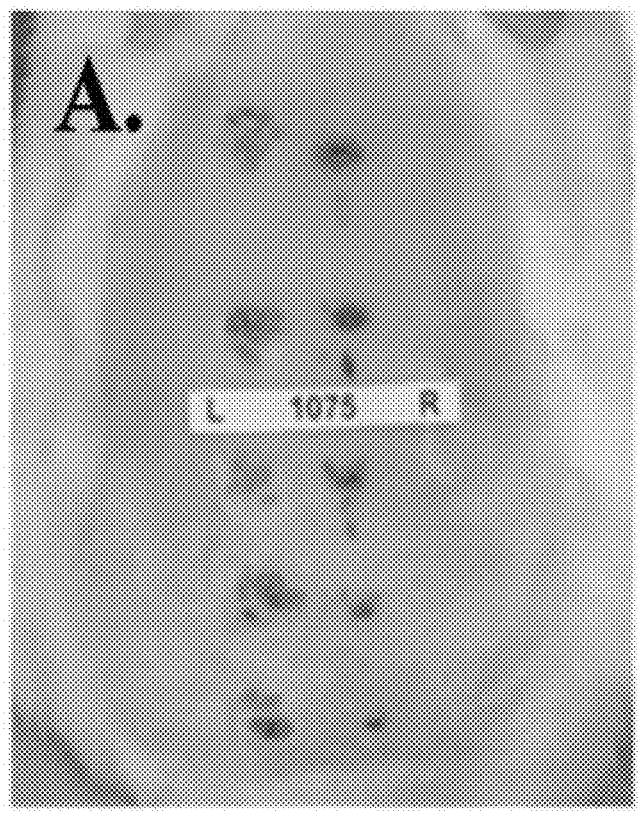
FIG. 3. Rabbit Skin Model of Papilloma Virus Infection.

Cloning of 8 Genes (E6, E7, E1, E2, E4, E5, L2, and L1) from HPV16, 18, 6 and 11 in Luciferase Expression Vector to Make Fusion Genes HPV16, 18, 6 and 11 genes were cloned into psi-CHECK1/2 vector (FIG. 2. produced by Promega, a dual luciferase system with build-in internal luciferase control system). XhoI and EcoRI restriction enzyme sites were added in the 5' and 3' and of PCR amplified genes, and fused to the luciferase gene in the same open reading frame (ORF). Each construct harbors one or more genes depending on the size of the genes. After cloning, the constructed plasmids were used to transfect HeLa cells and permanently integrate the genes into the chromosomes to get stable cell lines. As an alternative, each construct could also be used in transient transfection together with the siRNAs for testing of gene expression knocking down (silencing) by siRNA. After the establishment of the cell line, a time course of Renilla luciferase activity was titrated. Then the specific gene knock-down was evaluated by the luciferase expression level. If transient transfection system was used, then co-transfection or stepwise transfection was applied with siRNA designed for screening by luciferase assay with proper controls.

Screen siRNAs in Cell Lines Harboring HPV Genes

SiHa is a cervical carcinoma cell line harboring HPV16 genome and expressing oncoproteins E6 and E7 [25, 26]. SiHa cell line was used to screen the function of siRNAs targeting E6 and E7 genes in the strain of HPV16. SiHa cells was grown in RPMI 1640 medium supplemented with 10% FCS, 2 mM L-glutamine, 100 U/ml penicillin, 100 µg/ml streptomycin, 100 µM non-essential amino acids, 1 mM sodium pyruvate, 50 µM 2-ME, 400 µg/ml G418 and 10% NCTC-109 medium at 37° C. with 10% $CO_2$. The cells were transfected with siRNAs complexed with LipofectAmine 2000 according to manufacturer's instruction. The cells were harvested and qRT-PCR was applied to evaluate the gene expression level of E6 and E7. The same cell samples were applied for ELISA and Western analysis.

Similarly, HeLa cervical carcinoma cell which has HPV18 genome integrated in the cellular genome [27] was used to screen siRNAs targeting HPV18 genes' expression. The cells were grown in the medium similarly described in above section. The siRNA transfection, qRT-PCR, ELISA and Western were followed the same procedures.

For siRNAs targeting HPV6 and 11, the screen was applied HPV6b cDNA-based C33A (non-cervical carcinoma) cell line [28]. The cells were grown in the medium described above. The siRNA transfection, qRT-PCR, ELISA, and Western will follow the procedure described in the previous section.

Validation of siRNA Cocktail in Cell Line
In Vitro Transfection of siRNA

SiHa cells, maintained in Dulbecco's Minimal Essential Medium (DMEM) containing 10% fetal calf serum (FCS) and 20 mM glutamine, were examined for the ability of individual siRNAs to knock down particular gene targets. Cells were transfected using a Lipofectamine 2000 (Invitrogen, CA). Briefly, the cells were seeded (1×105 per well) in a 6-well plate in 2 ml of DMEM medium. The siRNA was diluted in 0.2 ml serum-free Opti medium mixed with 3 µl of the transfection reagent, incubated for 30 min at room temperature, then added drop-wise into the cell culture. Target mRNA and protein levels and effects on cells were analyzed in 48 h.

Screening siRNAs Against HPV16, 18, 6 and 11 Genes in HeLa229 by Measuring Luciferase Strength HeLa229 cell line (ATCC) has been co-transfected with the plasmids encoding the fusion gene of HPV viral gene and luciferase and each of correspondent siRNA. In the controls, the vector with only the luciferase, or the fusion gene co-transfected with un-related siRNAs were used. The luciferase strength is measured in all the samples to screen the most active siRNA molecules which can knock down the expression of luciferase. After luciferase assays, the same samples were applied for RT-PCR, ELISA and Western analysis. After screening analysis, two siRNAs for each gene in HPV16, 18, 6 and 11 will be selected for the combination and in vivo studies (below).

Screen siRNAs in Cell Lines Harboring HPV Genes

SiHa is a cervical carcinoma cell line harboring HPV16 genome and expressing oncoproteins E6 and E7 [25, 26]. SiHa cells were used to screen the function of siRNAs targeting E6 and E7 genes in the strain of HPV16. SiHa cells were grown in RPMI 1640 medium supplemented with 10% FCS, 2 mM L-glutamine, 100 U/ml penicillin, 100 µg/ml streptomycin, 100 µM non-essential amino acids, 1 mM sodium pyruvate, 50 µM 2-ME, 400 µg/ml G418 and 10% NCTC-109 medium at 37° C. with 10% $CO_2$. The cells were transfected with siRNAs complexed with LipofectAmine 2000 according to manufacturer's instruction. The cells were harvested and qRT-PCR was applied to evaluate the gene expression level of E6 and E7. The same cell samples were also applied for ELISA and Western analysis.

Similarly, HeLa cervical carcinoma cell, which has HPV18 genome integrated in the cellular genome [27], was used to screen siRNAs targeting HPV18 genes' expression. The cells were grown in the medium similarly described in above section. The siRNA transfection, qRT-PCR, ELISA and Western were followed the same procedures.

Gene Knock-Down Assay by RT-PCR Analysis

The gene knockdown results can be evaluated by measuring the mRNA changes within siRNA treated cells using RT-PCR to amplify RNA isolated from corresponding cells. Selection of the appropriate upstream and downstream primers is the initial step for evaluation of targeted gene knock-down and choice of the appropriate cell lines. The sequences of the primers for RT-PCR analysis are:

```
HPV16 PCR primer list
HPV16-1:
16E6-1F (191-461):    GGAATCCATATGCTGTATGT    PCR length: 270 bp
                      (SEQ ID NO: 5)

16E6-1B (191-461):    CTACGTGTTCTTGATGATCT
                      (SEQ ID NO: 6)

HPV16-2:
16E6-2F (278-448):    CAACATTAGAACAGCAATAC    PCR length: 170 bp
                      (SEQ ID NO: 7)

16E6-2B (278-448):    ATGATCTGCAACAAGACATA
                      (SEQ ID NO: 8)

HPV16-E7-1:
16E7-1F (21-43):      ATTGCATGAATATATGTTAGATT PCR length: 250 bp
                      (SEQ ID NO: 9)

16E7-1B (248-270):    CACAATTCCTAGTGTGCCCATTA
                      (SEQ ID NO: 10)

HPV18 PCR primer list
HPV18-1:
18E6-1F (65-84):      ACACTTCACTGCAAGACATA    PCR length: 196
                      (SEQ ID NO: 11)

18E6-1B: (241-260):   CCATACACAGAGTCTGAATA
                      (SEQ ID NO: 12)

HPV18-2:
18E6-2F (107-126):    AGACAGTATTGGAACTTACA    PCR length: 151
                      (SEQ ID NO: 13)

18E6-2B (238-257):    TACACAGAGTCTGAATAATG
                      (SEQ ID NO: 14)

HPV18-E7-1:
18E7-1F (38-54):      TGCATTTAGAGCCCCAA       PCR length: 253
                      (SEQ ID NO: 15)

18E7-1B (275-291):    CACAAAGGACAGGGTGT
                      (SEQ ID NO: 16)
```

Total RNA was extracted from cell culture or tumor tissues with RNeasy mini kit (Qiagen, Valencia, Calif.) according to the manufacturer's instructions. For RT-PCR, the first cDNA strands were synthesized by using cDNA Synthesis Kit (GE Healthcare, Chicago, Ill.) according to the manufacturer's instructions. The PCR reaction was started with lower cycle numbers, from 25, 30 to 35 to avoid the possible amplification plateau. Both Geneamp 9700 Thermalcycler and Taqman (ABI, CA) were used for PCR analysis. The amplicons were subjected to the gel electrophoresis analysis.

ELISA Assay for Luciferase Expression

The HPV gene expression after siRNA knock down could be evaluated by the protein level assay of Luciferase through Enzyme Linked Immunosorbent Assay (ELISA), since all the HPV gene were fused with luciferase gene. The same samples were applied for ELISA assays for Luciferase.

ELISA with specific antisera will be used for validation of siRNA-mediated down-regulation targeted proteins according to the manufacturer's instructions. Antibodies against Luciferase will be purchased from Promega.

Western Analysis for Luciferase Expression

The HPV gene expression after siRNA knocking down was evaluated by Western analysis against HPV16-E7. The same samples used in the above assays were applied to Western analysis to evaluate gene down regulation by each specific siRNA molecule. Antibodies against HPV16-E7 were purchased from Promega.

SiRNA Cocktail

The most potent siRNA to down regulate each gene in HPV will be grouped to evaluate the function to knock-down several genes' expression within each of species of HPV16, 18, 6 and 11. Following that, a complex to include siRNAs targeting all 4 HPV species will be formed to get the final cocktail to target either early or late genes in HPV16, 18, 6 and 11.

SiRNA Duplex with Potency Enhancer Motif

The siRNA molecules with Potency Enhancer Motif (PEM) will be compared with other siRNA molecules in Luciferase assay, RT-PCR, ELISA and Western.

Selection of siRNAs with and without PEM Sequence

In our siRNA design, L2 and L1 from HPV16 have 2 and 1 siRNAs with PEM sequence, respectively. While in HPV18, E6, E7, E1, and L1 each have 2, 1, 3, and 3 siRNAs with PEM sequence (Table 1 and 2). Special attention will be paid to those genes and siRNAs. If the in vitro cell screening showed acceptable effectiveness of the siRNAs to inhibit designated gene inhibition, those siRNAs will be paired with the ones without PEM but target the same gene for further animal studies.

Validation of siRNA Cocktail Complexed with Dendrimer in a Rabbit Model

Dendrimer Selection

The anionic poly-(L-Lysine) dendrimer (PAMAM, the active ingredient of VivaGel®) was used to complex with selected siRNA duplexes. dendrimer alone or siRNA alone was compared with the complex of dendrimer and siRNAs at different ratios. Each designed group was applied in the cottontail rabbit model [24].

Complex of siRNAs with Dendrimer

Selected siRNA were formulated with dendrimer in the ratio found above. The testing condition in the animal included the dendrimer alone and siRNA alone as control. Non-relevant siRNA was also used as control.

Since the active ingredient of VivaGel® is an anionic poly-(L-Lysine), the ratio of siRNA with dendrimer was tested to reach the optimum surface charge of the complex so that the VivaGel® is still active as proved in other experiments. Non-relevant siRNA with similar charge was formulated with VivaGel® as control.

Therapeutic Program Verses Prophylactic Program

In the therapeutic program, the siRNA was applied on the animal skin after the virus was inoculated. While in the prophylactic program, siRNA was applied prior to the inoculation of the HPV virus. The time interval was tested to find the best time point to apply "prophylactic" siRNAs on the animals before the virus challenge.

Specifically, for example, if siRNA #231 and 232 (each with the PEM sequence) and #194 and 258 (both without PEM sequence) in HPV16 showed effectiveness in inhibiting HPV16 L2 gene expression in cell screening, the pair of #231 and 194, or the pair of #232 and 258, or the pair of #231 and 258, or the pair of #232 and 194 will be selected for further therapeutic and prophylactic studies. In both studies, each pair was applied on one rabbit. The siRNA with PEM (e.m. #231) and without PEM (e.m. #194) was applied on left and right side of the animal respectively, with increased dose (from 5 μg to 100 μg), and proper control. The virion particle was inoculated on the same spot prior to the siRNA for the treatment program, or after the application of siRNA for prophylactic program. The interval between two treatments was tested in a separate experiment to cover from 4 hours to 72 hours.

Chimeric HPV Virion Particle Preparation

Using pseudovirion technology, we produced infectious particles composed of a heterologous cottontail rabbit Papilloma virus (CRPV) genome encapsulated with HPV16/18 or CRPV capsid proteins [29]. The CRPV genome contains the simian virus 40 (SV40) origin of replication (337 bp) cloned at the BglII site within the upstream regulatory region for improved CRPV genome amplification in the packaging cell line 293TT. Both homologous (CRPV capsid/CRPV genome) and chimeric (HPV16 or 18 capsid/CRPV genome) Papilloma virion particles will be prepared according to the methods [29]. The virion particle prepared this way is infectious in vitro at low volume (<10 μl) to induce epidermal papilloma on New Zealand White rabbits [24].

Rabbit Skin Inoculation of HPV Virus and Treat with Complex of siRNA and Dendrimer We used the established cottontail rabbit model [24] to test the efficacy of our siRNA and the complex of siRNA and dendrimer to inhibit the lesion formation on the animal skin (FIG. 3). Briefly, the siRNAs, dendrimer, and the formulated complex of siRNA and dendrimer were applied on three groups of six rabbit each in various amounts (5 μg to 100 μg), before or after the virus inoculation depending on the program used to test the efficacy. Four days after the final treatment, blood samples were collected for analysis of capsid-specific antibody by using an enzyme-linked immunosorbent assay (ELISA). Each serum sample was tested for the ability to bind CRPV, HPV16 and HPV18 L1-only virus-like particles (VLPs) adhered overnight on 96-well plates in PBS (pH 7.4) at 4° C.

Validation of siRNA Cocktail Complexed with HK Polymer in a Rabbit Model

HK Polymer Selection

H2K4b is a histidine-lysine polymer with MW of 11,137, and showed the highest activity to inhibit the growth of fugal strains, *C. albicans* and *C. kefyr* [18]. The structure of H2K4b is shown here:

```
KKK(KHKHHKHHKHHKHHHKHHKHK)4
(core sequence disclosed as SEQ ID NO: 1)
```

Because of its anti-fungus activity, H2K4b will be selected as the HK polymer to formulate with the designed siRNAs against HPV16, 18, 6 and 11.

Complex of siRNAs with HK Polymer

Selected siRNA were formulated with HK polymer in the ratio found as described above. The testing condition in the animal included the HK polymer alone and siRNA alone as a control. Non-relevant siRNA was also used as a control.

The ratio of siRNA with HK Polymer was tested to reach the optimum surface charge for efficient cell delivery. Non-relevant siRNA with similar charge was formulated with HK polymer as control.

Rabbit Skin Inoculation of HPV Virus and Treat with Complex of siRNA and HK Polymer We used the established cottontail rabbit model [24] to test the efficacy of our siRNA and the complex of siRNA and HK polymer to inhibit the lesion formation on the animal skin (FIG. 3). Briefly, the siRNAs, HK polymer, and the formulated complex of siRNA and HK polymer were applied on three groups of six rabbit each in various amounts (5 μg to 100 μg), before or after the virus inoculation, depending on what program were used to test the efficacy. Four days after the final treatment, blood samples were collected for analysis of capsid-specific antibody by using an enzyme-linked immunosorbent assay (ELISA). Each serum sample was tested for the ability to bind CRPV, HPV16 and HPV18 L1-only virus-like particles (VLPs) adhered overnight on 96-well plates in PBS (pH 7.4) at 4° C.

Example 1

25 mer siRNA is More Potent than 21 mer siRNA

Although initial studies mostly applied 19mer and 21mer siRNA duplexes, several lines of evidence showed that 23mer, 25mer and 27mer siRNA duplexes exhibited more potent silencing effects than 19mer and 21mer siRNAs did. We found that 25mer duplexes with blunt ends are the most potent inhibitors. We have tested a 25mer siRNA duplex targeting human VEGF gene, hVEGF-25c (sense: 5'-CACAACAAAUGUGAAUGCAGACCAA-3' (SEQ ID NO: 17); Antisense: 5'-UUGGUCUGCAUUCACAUUUGUUGUG-3' (SEQ ID NO: 18)), comparing it to a 21mer siRNA duplex, which has been tested many times as one of the most potent VEGF specific inhibitory duplexes, hVEGF-21a (sense: 5'-UCGAGACCCUGGUGGACAUTT-3' (SEQ ID NO: 19); antisense: 5'-AUGUCCACCAGGGUCUCGATT-3' (SEQ ID NO: 20)), in the cell culture followed with Q-RT-PCR analysis (FIG. 4A). A similar study also was carried out with ELISA analysis for the difference between the 25 mer and 21 mer siRNA both targeting VEGF (FIG. 4B).

Example 2

Cell Lines and PCR Primers for Potent siRNA Screening

SiHa cells which host HPV16 genes was chosen as the in vitro cell model to screen siRNAs against E7 gene expression in both HPV16 and chimerical human rabbit papilloma virus. Transfected SiHa cells were also applied in Western to evaluate the E7 protein expression. HeLa cells which host HPV18 genes was chosen as the in vitro cell model to screen siRNAs against E7 gene expression in HPV18. Quantitative RT-PCR was used to evaluate the E7 gene expression for potent siRNA screening.

PCR primers used to monitor the E7 gene expression in SiHa cell line:

```
16E7-Forward:      ATTGCATGAATATATGTTAGATT
                   (SEQ ID NO: 9)

16E7-Reverse:      CACAATTCCTAGTGTGCCCATTA;
                   (SEQ ID NO: 10)
```

PCR primers used to monitor the E7 gene expression in HeLa cell line:

```
18E7-1Forward:     TGCATTTAGAGCCCCAA
                   (SEQ ID NO: 15)

18E7-1Reverse:     CACAAAGGACAGGGTGT.
                   (SEQ ID NO: 16)
```

Example 3

Design and Screen Small Interfering RNAs (siRNAs) Against E7 Gene in HPV16

The following are the DNA sequences in HPV16 E7 gene corresponding to each of the siRNA molecule. They all qualified in our in silica design system, and used as the model for siRNA syntheses.

```
Rec#, 34,     GCATGGAGATACACCTACATTGCAT,
              (SEQ ID NO: 21)

Rec#, 37,     GGACAGAGCCCATTACAATATTGTA,
              (SEQ ID NO: 22)

Rec#, 39,     GCAAGTGTGACTCTACGCTTCGGTT,
              (SEQ ID NO: 23)

Rec#, 40,     GCGTACAAAGCACACACGTAGACAT,
              (SEQ ID NO: 24)

Rec#, 41,     CGTACAAAGCACACACGTAGACATT,
              (SEQ ID NO: 25)

Rec#, 42,     GCACACACGTAGACATTCGTACTTT,
              (SEQ ID NO: 26)

Rec#, 43,     GGAAGACCTGTTAATGGGCACACTA,
              (SEQ ID NO: 27)

Rec#, 44,     CCTGTTAATGGGCACACTAGGAATT,
              (SEQ ID NO: 28)
```

Figure 4A:
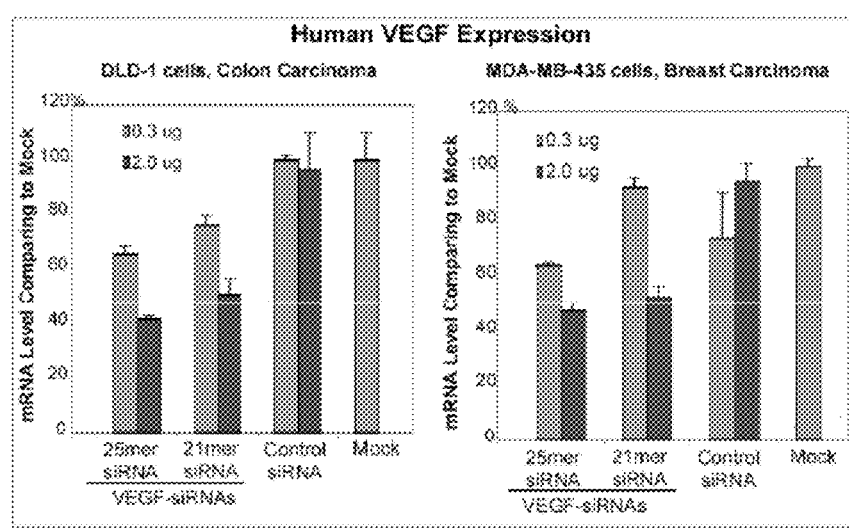
FIG. 4A. 25 mer siRNA is more potent than 21 mer siRNA.
Figure 4B:
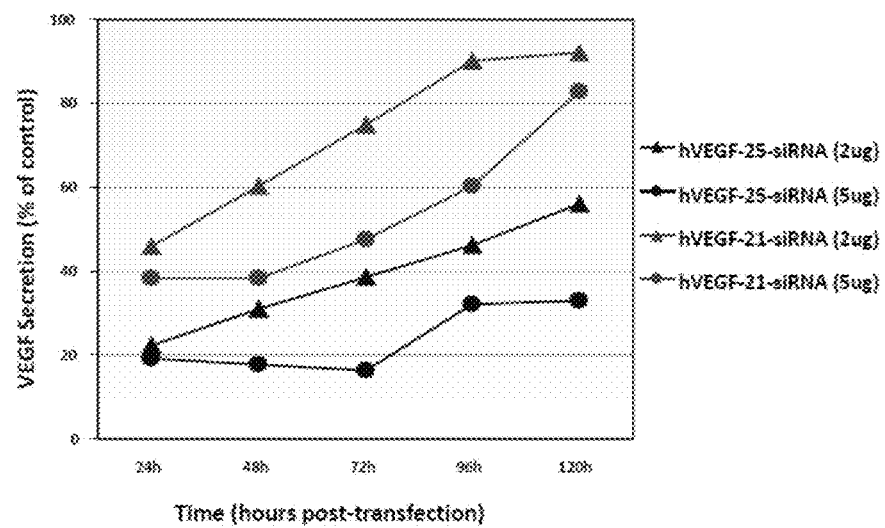
FIG. 4B. 25 mer siRNA is more potent than 21 mer siRNA.

Through the in vitro SiHa cell screening, it showed that 4 out of 8 siRNAs reduced the E7 gene expression over 80% (FIG. 4).

Example 4

Construction of Chimerical Human Rabbit Papilloma Virus (cH-RPV)

Figure 5:
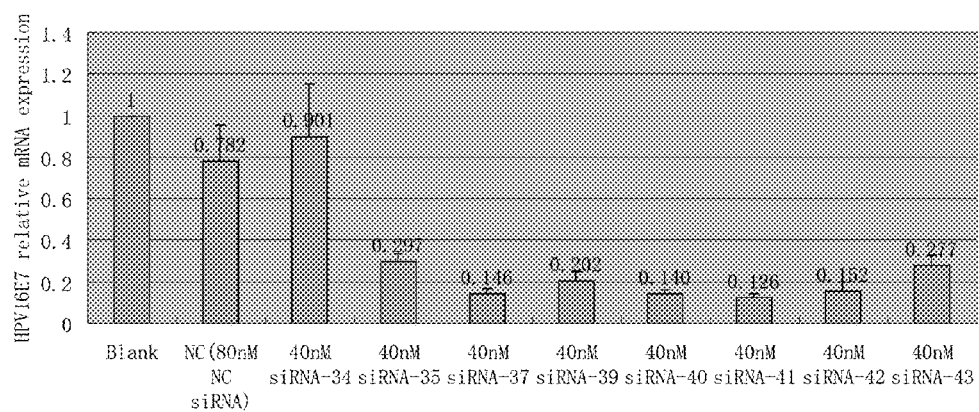
FIG. 5. HPV16 E7 Expression Knocking Down by siRNAs in SiHa Cells.

Three epitopes (A, B and C in FIG. 5 top) from HPV16 E7 gene were applied to construct hybrid E7 gene between CRPV and HPV16. Epitope A corresponds to amino acid 82 to 90, while Epitope B corresponds to amino acid 49 to 57, and Epitope C corresponds to amino acid 11 to 20. The sequences were inserted at the end of CRPVE7 before the stop codon in the same open reading frame (ORF) to form a hybrid protein of E7 as shown (FIG. 5, bottom).

The potency of each of the hybrid viruses to form papilloma was confirmed in the rabbit skin.

Example 5

Design and Screen Small Interfering RNAs (siRNAs) Against E7 Gene in cH-RPV (Chimerical Human Rabbit Papilloma Virus)

```
CRPE7-36    5'- GCAUGAAUAUAUGUUGGAUCUGCA-3'
            (SEQ ID NO: 29)

CRPE7-37    5'- GGACAGAGCCCACUACAACAUCGU-3'
            (SEQ ID NO: 30)

CRPE7-38    5'- GCCCACUACAACAUCGUGACCUUUU-3'
            (SEQ ID NO: 31)

CRPE7-43    5'- GGAAGACCUGCUGAUGGGCACCCU-3'
            (SEQ ID NO: 32)

CRPE7-44    5'- CCUGCUGAUGGGCACCCUGGGCAU-3'
            (SEQ ID NO: 33)

CRPE7-45    5'- GCACCCUGGGCAUCCUGUGCCCCAU-3'
            (SEQ ID NO: 34)
```

Six siRNA shown above designed to target the three epitopes in the hybrid E7 gene, with CRPE7-36 targeting Epitope C, CRPE7-37 and CRPE7-38 targeting Epitope B, and CRPE7-43, -44 and -45 targeting Epitope A.

Figure 6:
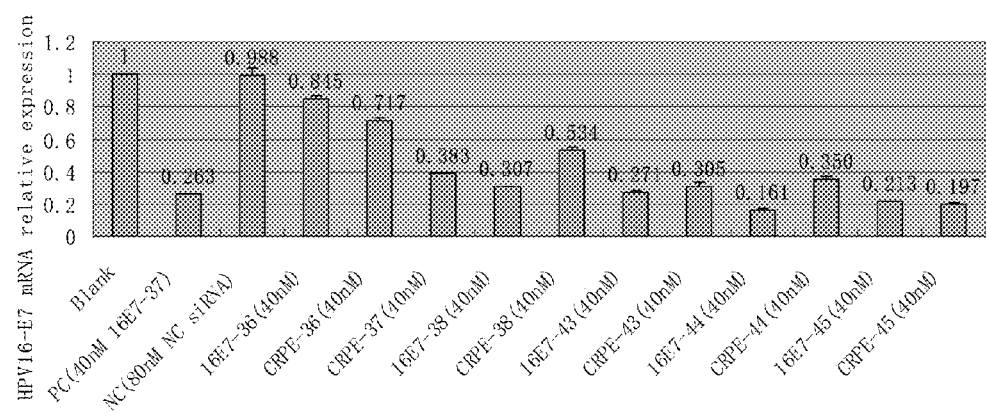
FIG. 6. HPV16 E7 Expression Knocking Down by CRPV Hybrid siRNAs in SiHa Cells.

The results in FIG. 6 have shown that 4 of the hybrid siRNAs were able to reduce E7 gene expression over 60%, with #45 as the most potent siRNA which knocked-down E7 gene expression over 80%. The potency is listed as, 45 (0.197)>43 (0.305)>44 (0.350)>37 (0.383). The numbers in parentheses are the expression of E7 gene comparing with negative control.

Example 6

Design Small Interfering RNAs (siRNAs) Against E7 Gene in HPV18

The following are the siRNA sequences against corresponding sequences in HPV18 E7 gene. They all qualified in our in silica design system.

```
HPV18E7-31:    5'- GCAUGGACCUAAGGCAACAUUGCAA-3'
               (SEQ ID NO: 35)

HPV18E7-34:    5'- GGUUGACCUUCUAUGUCACGAGCAA-3'
               (SEQ ID NO: 36)
```

```
HPV18E7-36:    5'- GCAAUUAAGCGACUCAGAGGAAGAA-3'
               (SEQ ID NO: 37)

HPV18E7-38:    5'- CGAUGAAAUAGAUGGAGUUAAUCAU-3'
               (SEQ ID NO: 38)

HPV18E7-39:    5'- CGAGCCGAACCACAACGUCACACAA-3'
               (SEQ ID NO: 39)

HPV18E7-43:    5'- GCCAGAAUUGAGCUAGUAGUAGAAA-3'
               (SEQ ID NO: 40)

HPV18E7-44:    5'- GCUCAGCAGACGACCUUCGAGCAUU-3'
               (SEQ ID NO: 41)

HPV18E7-46:    5'- GCUGUUUCUGAACACCCUGUCCUUU-3'
               (SEQ ID NO: 42)
```

Figure 7:
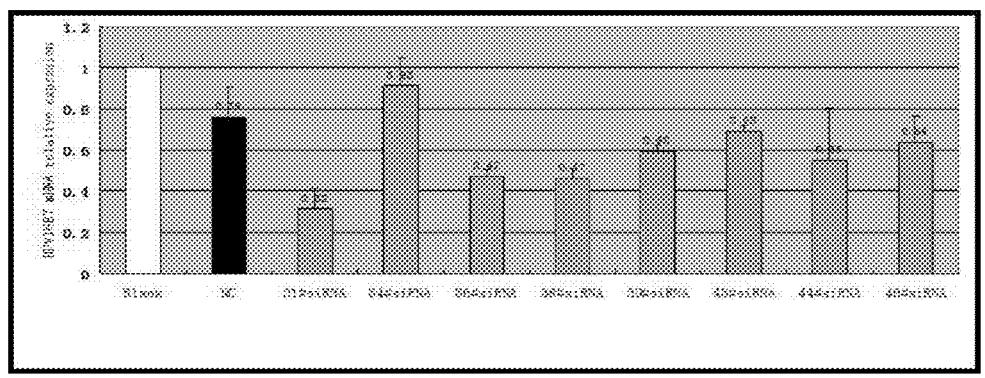
FIG. 7. The effect of the first batch siRNAs on knocking-down of HPV18E7 mRNA expression.

Through the in vitro HeLa cell screening, it showed that 3 out of 8 siRNAs (#31, #36, and #38) are able to reduce the E7 gene expression over 50% (FIG. 7).

Example 7

Screen Small Interfering RNAs (siRNAs) Against E7 Gene in HPV18

FIG. 7 shows the effect of the designed siRNAs on knocking-down of HPV18E7 mRNA expression. The transfections was done on HeLa cells, using 40 nM as the action concentration, and the 80 nM negative control siRNA as the NC group. β-actin was used as the internal control gene. Mean±SD.

The results demonstrated that three siRNAs (31#, 36#, 38#) showed fine knocking-down effect (>50%) targeting HPV16E7 mRNA expression. These three siRNAs were applied for the EC50 experiment.

Example 8

Figure 8:
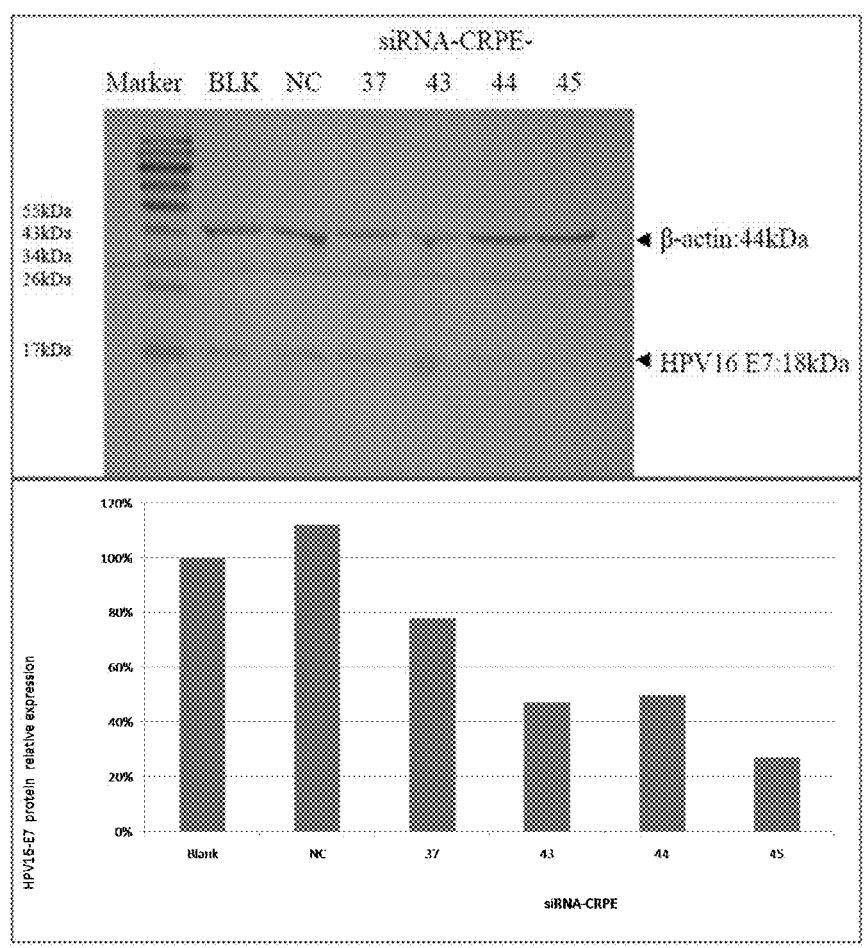
FIG. 8. The potent siRNAs are capable of reducing the E7 gene expression in the SiHa cell line. Four siRNAs against the hybrid E7 gene were further tested for their ability to reduce the E7 protein expression in SiHa cells. The Western blot (top) and quantitative data (bottom) showed that the potency of the siRNA reducing the E7 protein expression are listed in this order, -45>-43>-44>-37, which fit the results in the qRT-PCR experiment.

Western Analysis to Confirm the Knocking Down of E7 Protein Expression by Potent siRNAs Four siRNAs against the hybrid E7 gene were further tested for their ability to reduce the E7 protein expression in SiHa cells by Western analysis. In FIG. 8, The Western blot (top) and quantitative data (bottom) showed that the potency of the siRNA reducing the E7 protein expression are listed in this order, -45>-43>-44>-37, which fit the results in the qRT-PCR.

Example 9

Testing the Efficacy of the siRNAs in Skin Infection Rabbit Animal Model (SIRAM)

Figure 9:
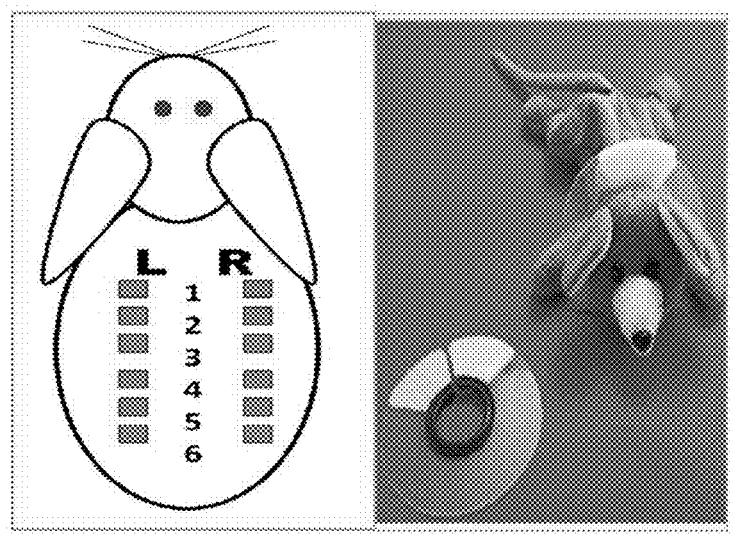
FIG. 9. Rabbit skin inoculated with different papilloma virus, and treated with different siRNA-HKP paste (L). Elizabethan collars were applied to the animals to prevent disturbance of the treated area by the animal (R).

CRPV/NZW rabbit in the testing In order to test the therapeutic efficacy of the siRNA we have confirmed with our in vitro cell screening system, 6 different wild type and hybrid viruses were inoculated on the NZW rabbit skin as illustrated in FIG. 9. Elizabeth collars (FIG. 9, right) were worn by each animal to avoid disturbing of the treated area by the animals.

In the pilot study six animals were used in the experiments. In each animal, L1-R1, L2-R2, L3-R3, L4-R4, L5-R5 and L6-R6 were challenged with six different constructs respectively as illustrated in the FIG. 7 legends. Two weeks after the challenge, the left sites of the papillomas were treated with corresponding testing siRNAs, N.C siRNA and Cidovofir topically for five consecutive days. Papilloma outgrowth began to be monitored at week 3 and until the termination of the experiment at the end of week 5. Pictures were also taken for record. Right sites are untreated control for the left treated sites. If the siRNA is effective, we should see smaller or no papillomas on the left sites but not on the right sites. The construct that infected L5-R5 sites is more vigorous than those on sites L2-R2, L3-R3 and L4-R4. L1-R1 infected with wild-type CRPV is used as a specificity control for the SiRNA. Therefore, if an epitope specific siRNA is effective, it should not influence L1-R1 sites but the sites that challenged with the constructs containing this epitope such as L5-R5.

The viruses are described in the following:
L1-R1, wt CRPV DNA 5 ug/site;
L2-R2, CRPV with HPV16E7/A 82-90 insert;
L3-R3, CRPV with HPV16E7/B 45-57 insert;
L4-R4, CRPV with HPV16E7/C 11-20 insert;
L5-R5, CRPV with HPV16 E7/82-90 at L2 insert;
L6-R6, CRPV tandem repeat with HPV16E7.

Figure 10:
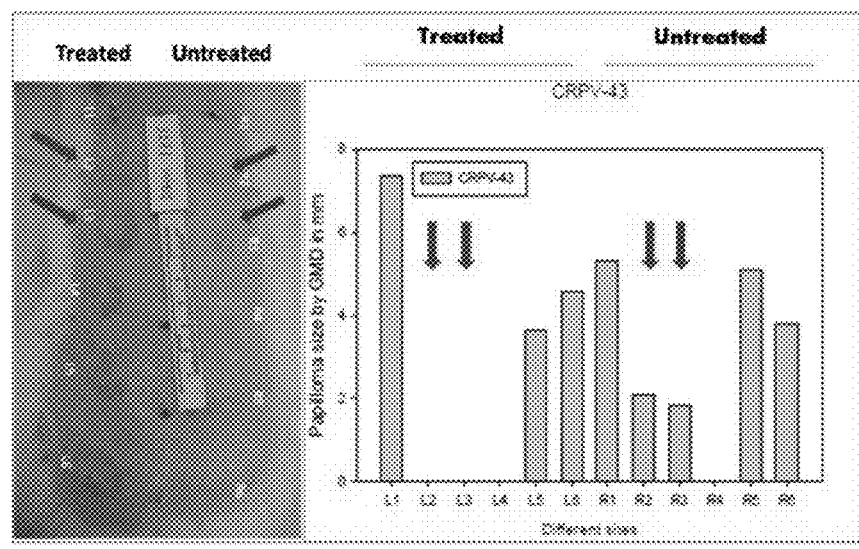
FIG. 10. SiRNA (siNA-CRPV-43) treatment inhibited the skin warts growth induced by cH-RPV in the rabbit model (L), data (R).

After papilloma appeared on the skin, we applied different siRNAs to the papilloma to evaluate the efficacy of them 2 weeks after the viral challenge. The following are the siRNAs applied on the animals:
Rabbit #3270, siRNA-CRPC-37;
Rabbit #3271, siRNA-CRPC-43;
Rabbit #3272, siRNA-CRPC-44;
Rabbit #3273, siRNA-CRPC-45;
Rabbit #3274, siRNA-NC;
Rabbit #3275, Cidofovir, the positive control;

In one of the examples, CRPV-43 treatment inhibited the papilloma growth (FIG. 10).

The ability of the siRNAs against the hybrid human rabbit papilloma growth was summarized in FIG. 11.

REFERENCES

1. Gissmann, L. and H. Z. Hausen, Human papilloma virus DNA: physical mapping and genetic heterogeneity. Proc Natl Acad Sci USA, 1976. 73(4): p. 1310-3.
2. Bantel-Schaal, U. and H. zur Hausen, Characterization of the DNA of a defective human parvovirus isolated from a genital site. Virology, 1984. 134(1): p. 52-63.
3. Crawford, L., Papilloma viruses and cervical tumours. Nature, 1984. 310(5972): p. 16.
4. Gissmann, L., et al., Presence of human papillomavirus in genital tumors. J Invest Dermatol, 1984. 83(1 Suppl): p. 26s-28s.
5. Kahn, J. A., HPV vaccination for the prevention of cervical intraepithelial neoplasia. N Engl J Med, 2009. 361(3): p. 271-8.
6. Information from FDA and CDC on Gardasil and its Safety
7. Trottier, H. and A. N. Burchell, Epidemiology of mucosal human papillomavirus infection and associated diseases. Public Health Genomics, 2009. 12(5-6): p. 291-307.
8. Hellner, K., et al. HPV16 E7 oncogene expression in normal human epithelial cells causes molecular changes indicative of an epithelial to mesenchymal transition. Virology 2009 Aug. 15 [cited 391 1]; 2009 Jun. 26: [57-63]. Available from: http://www.ncbi.nlm.nih.gov/entrez/query.fcgi?cmd=Retrieve&db=PubMed&dopt=Citation&list_uids=19552933.
9. Information from FDA and CDC on Gardasil and its Safety
10. http://www.fda.gov/BiologicsBloodVaccinesNaccines/ApprovedProducts/ucm172678.htm 11. Kohout T, Stewart A. "New Report Examines Laws that Would Mandate HPV Vaccine for Young Women". Jacobs Institute for Women's Health, George Washington University. http://www.jiwh.org/content.cfm?sectionid=167
12. "1 in 4 US teen girls got cervical cancer shot". http://www.washingtonpost.com/wp-dyn/content/article/2008/10/09/AR2008100901452.html?sub=new
13. Cervarix Marketing in Kenya
14. "Information from FDA and CDC on Gardasil and its Safety"
15. Menjoge, A. R., R. M. Kannan, and D. A. Tomalia, Dendrimer-based drug and imaging conjugates: design considerations for nanomedical applications. Drug Discov Today. 15(5-6): p. 171-85.
16. http://www.clinicaltrials.gov
17. http://www.starpharma.com/data/080421%20SPL7013%20Inhibits%20Clinically%20Relevant%20Strains%20of%20HPV.pdf#search="HPV"
18. Zhu, J., et al., Synthetic histidine-rich peptides inhibit *Candida* species and other fungi in vitro: role of endocytosis and treatment implications. Antimicrob Agents Chemother, 2006. 50(8): p. 2797-805.
19. Sharp, P. A., RNA interference—2001. Genes Dev, 2001. 15(5): p. 485-90.
20. Li, L. and Y. Shen, Overcoming obstacles to develop effective and safe siRNA therapeutics. Expert Opin Biol Ther, 2009. 9(5): p. 609-19.
21. http://www.clinicaltrials.gov/ct2/results?term=siRNA
22. L1, B. J., et al., Using siRNA in prophylactic and therapeutic regimens against SARS coronavirus in Rhesus macaque. Nat Med, 2005. 11(9): p. 944-51.
23. Xie, F. Y., M. C. Woodle, and P. Y. Lu, Harnessing in vivo siRNA delivery for drug discovery and therapeutic development. Drug Discov Today, 2006. 11(1-2): p. 67-73.
24. Mejia, A. F., et al., Preclinical model to test human papillomavirus virus (HPV) capsid vaccines in vivo using infectious HPV/cottontail rabbit papillomavirus chimeric papillomavirus particles. J Virol, 2006. 80(24): p. 12393-7.
25. Gunn, G. R., et al., Two *Listeria monocytogenes* vaccine vectors that express different molecular forms of human papilloma virus-16 (HPV-16) E7 induce qualitatively different T cell immunity that correlates with their ability to induce regression of established tumors immortalized by HPV-16. J Immunol, 2001. 167(11): p. 6471-9.
26. de Wilde, J., et al., hTERT promoter activity and CpG methylation in HPV-induced carcinogenesis. BMC Cancer. 10: p. 271.
27. Thierry, F., Transcriptional regulation of the papillomavirus oncogenes by cellular and viral transcription factors in cervical carcinoma. Virology, 2009. 384(2): p. 375-9.
28. Donne, A. J., et al., Effects of cidofovir on a novel cell-based test system for recurrent respiratory papillomatosis. Head Neck, 2007. 29(8): p. 741-50.
29. Culp, T. D., et al., Papillomavirus particles assembled in 293TT cells are infectious in vivo. J Virol, 2006. 80(22): p. 11381-4.

All publications, including issued patents and published patent applications, and all database entries identified by url addresses or accession numbers are incorporated herein by reference in their entirety.

Although this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

TABLE 1

HPV16 Sequences Corresponding to the siRNAs Against 8 Genes (Potency Enhancer Motif, PEM, is underlined and in bold font) HPV16 - 8siRNA

| Gene = "E6" (83 → 559) | |
|---|---|
| #8, | CCCACAGGAGCGACCCAGAAAGTTA (SEQ ID NO: 43) |
| #10, | CGACCCAGAAAGTTACCACAGTTAT (SEQ ID NO: 44) |
| #11, | CCACAGTTATGCACAGAGCTGCAAA (SEQ ID NO: 45) |
| #15, | CGACGTGAGGTATATGACTTTGCTT (SEQ ID NO: 46) |
| #19, | GGGAATCCATATGCTGTATGTGATA (SEQ ID NO: 47) |
| #22, | GCAATACAACAAACCGTTGTGTGAT (SEQ ID NO: 48) |
| #28, | CGGTGGACCGGTCGATGTATGTCTT (SEQ ID NO: 49) |
| #30, | CGATGTATGTCTTGTTGCAGATCAT (SEQ ID NO: 50) |
| Gene = "E7" (562 → 858) | |
| #34, | GCATGGAGATACACCTACATTGCAT (SEQ ID NO: 21) |
| #37, | GGACAGAGCCCATTACAATATTGTA (SEQ ID NO: 22) |
| #39, | GCAAGTGTGACTCTACGCTTCGGTT (SEQ ID NO: 23) |
| #40, | GCGTACAAAGCACACACGTAGACAT (SEQ ID NO: 24) |
| #41, | CGTACAAAGCACACACGTAGACATT (SEQ ID NO: 25) |
| #42, | GCACACACGTAGACATTCGTACTTT (SEQ ID NO: 26) |
| #43, | GGAAGACCTGTTAATGGGCACACTA (SEQ ID NO: 27) |
| #44, | CCTGTTAATGGGCACACTAGGAATT (SEQ ID NO: 28) |
| Gene = "E1" (865 → 2813) | |
| #51, | GGGTACGGGATGTAATGGATGGTTT (SEQ ID NO: 51) |
| #64, | CGGGTATGGCAATACTGAAGTGGAA (SEQ ID NO: 52) |
| #81, | GCTGCATTTGGACTTACACCCAGTA (SEQ ID NO: 53) |
| #92, | GGAGACACGCCAGAATGGATACAAA (SEQ ID NO: 54) |
| #97, | GGATTGTGCAACAATGTGTAGACAT (SEQ ID NO: 55) |

TABLE 1-continued

HPV16 Sequences Corresponding to
the siRNAs Against 8 Genes
(Potency Enhancer Motif, PEM,
is underlined and in bold font)
HPV16 - 8siRNA

| | |
|---|---|
| #107, | GGTGCAGCTAACACAGGTAAATCAT (SEQ ID NO: 56) |
| #118, | GGATGTAAAGCATAGACCATTGGTA (SEQ ID NO: 57) |
| #130, | CGATGGAGACTCTTTGCCAACGTTT (SEQ ID NO: 58) |

Gene = "E2" (2755 → 3852)

| | |
|---|---|
| #131, | GGAGACTCTTTGCCAACGTTTAAAT (SEQ ID NO: 59) |
| #135, | GCTATTTATTACAAGGCCAGAGAAA (SEQ ID NO: 60) |
| #146, | GGAAGTGCAGTTTGATGGAGACATA (SEQ ID NO: 61) |
| #151, | GGGTCAAGTTGACTATTATGGTTTA (SEQ ID NO: 62) |
| #155, | GGAAGTTCATGCGGGTGGTCAGGTA (SEQ ID NO: 63) |
| #163, | CGACCCATACCAAAGCCGTCGCCTT (SEQ ID NO: 64) |
| #167, | CCAAGATCAGAGCCAGACACCGGAA (SEQ ID NO: 65) |
| #172, | GGCATTGGACAGGACATAATGTAAA (SEQ ID NO: 66) |

Gene = "E4" (3332 → 3619)

| | |
|---|---|
| #158, | GCAACGAAGTATCCTCTCCTGAAAT (SEQ ID NO: 67) |
| #159, | CGAAGTATCCTCTCCTGAAATTATT (SEQ ID NO: 68) |
| #163, | CGACCCATACCAAAGCCGTCGCCTT (SEQ ID NO: 64) |
| #164, | GCCGTCGCCTTGGGCACCGAAGAAA (SEQ ID NO: 69) |
| #165, | GGCACCGAAGAAACACAGACGACTA (SEQ ID NO: 70) |
| #166, | GCACCGAAGAAACACAGACGACTAT (SEQ ID NO: 71) |
| #167, | CCAAGATCAGAGCCAGACACCGGAA (SEQ ID NO: 65) |

Gene = "E5" (3863 → 4099)

No sequence can be qualified.

Gene = "L2" (4235 → 5656)

| | |
|---|---|
| #192, | CGTGCATCGGCTACCCAACTTTATA (SEQ ID NO: 72) |
| #202, | GGGTACAGGCGGACGCACTGGGTAT (SEQ ID NO: 73) |

TABLE 1-continued

HPV16 Sequences Corresponding to
the siRNAs Against 8 Genes
(Potency Enhancer Motif, PEM,
is underlined and in bold font)
HPV16 - 8siRNA

| | |
|---|---|
| #217, | CCCAGATGTATCAGGATTTAGTATT (SEQ ID NO: 74) |
| #225, | CGCCCAGTGGCACGCCTAGGATTAT (SEQ ID NO: 75) |
| #232, | CC<u>ACTCC</u>CACTAAACTTATTACATA (SEQ ID NO: 76) |
| #247, | GCAGCCTCACCTACTTCTATTAATA (SEQ ID NO: 77) |
| #259, | CCAGGGTCTCCACAATATACAATTA (SEQ ID NO: 78) |

Gene = "L1" (5559 → 7154)

| | |
|---|---|
| #265, | GGCTGCCTAGTGAGGCCACTGTCTA (SEQ ID NO: 79) |
| #276, | GCTGGTTTGGGCCTGTGTAGGTGTT (SEQ ID NO: 80) |
| #283, | GCAGCAAATGCAGGTGTGGATAATA (SEQ ID NO: 81) |
| #289, | CCCATGTACCAATGTTGCAGTAAAT (SEQ ID NO: 82) |
| #301, | GGGTCTACTGCAAATTTAGCCAGTT (SEQ ID NO: 83) |
| #327, | GGAGGCACACTAGAAGATACTTATA (SEQ ID NO: 84) |
| #345, | CCTCATCTACCTCTACAACTGCTAA (SEQ ID NO: 85) |

TABLE 2

HPV18 Sequences Corresponding to
the siRNAs Against 8 Genes
(Potency Enhancer Motif, PEM, is
underlined and in bold font)
HPV18 - 8siRNA Gene = "E6" (105-581)

| | |
|---|---|
| #6, | GCAAGACATAGAAATAACCTGTGTA (SEQ ID NO: 86) |
| #7, | CCTGTGTATATTGCAAGACAGTATT (SEQ ID NO: 87) |
| #12, | CCCATGCTGCATGCCATAAATGTAT (SEQ ID NO: 88) |
| #18, | GGTGCCTGCGGTGCCAGAAACCGTT (SEQ ID NO: 89) |
| #21, | CCAGAAACCGTTGAATCCAGCAGAA (SEQ ID NO: 90) |
| #24, | GGGCACTATAGAGGCCAGTGCCATT (SEQ ID NO: 91) |

TABLE 2-continued

HPV18 Sequences Corresponding to the siRNAs Against 8 Genes (Potency Enhancer Motif, PEM, is underlined and in bold font) HPV18 - 8siRNA

| | | |
|---|---|---|
| #25, | CCGAGCACGACAGGAACGACTCCAA (SEQ ID NO: 92) | |
| #26, | GGAACGACTCCAACGACGCAGAGAA (SEQ ID NO: 93) | |

Gene = "E7" (590-907)

| | |
|---|---|
| #31, | GCATGGACCTAAGGCAACATTGCAA (SEQ ID NO: 94) |
| #34, | GGTTGACCTTCTATGTCACGAGCAA (SEQ ID NO: 95) |
| #36, | GCAATTAAGCGACTCAGAGGAAGAA (SEQ ID NO: 96) |
| #39, | CGAGCCGAACCACAACGTCACACAA (SEQ ID NO: 97) |
| #43, | GCCAGAATTGAGCTAGTAGTAGAAA (SEQ ID NO: 98) |
| #44, | GCTCAGCAGACGACCTTCGAGCATT (SEQ ID NO: 99) |
| #46, | GCTGTTTCTGAACACCCTGTCCTTT (SEQ ID NO: 100) |

Gene = "E1" (914-2887)

| | |
|---|---|
| #50, | GGGCACGGGTTGTAACGGCTGGTTT (SEQ ID NO: 101) |
| #69, | GGCAATGTATGTAGTGGCGGCAGTA (SEQ ID NO: 102) |
| #78, | GGGTTACAGCTATATTTGGAGTAAA (SEQ ID NO: 103) |
| #79, | GCTATATTTGGAGTAAACCCAACAA (SEQ ID NO: 104) |
| #104, | CCTTATTAGCAGACAGCAACAGCAA (SEQ ID NO: 105) |
| #130, | CGTGTTGGACATACTTTGATACCTA (SEQ ID NO: 106) |
| #142, | GGAAGAGGAAGATGCAGACACCGAA (SEQ ID NO: 107) |

Gene = "E2" (2817-3914)

| | |
|---|---|
| #144, | CGAAGGAAACCCTTTCGGAACGTTT (SEQ ID NO: 108) |
| #151, | GCAAGGGAACATGGCATACAGACAT (SEQ ID NO: 109) |
| #158, | GGAATACAGAACCTACTCACTGCTT (SEQ ID NO: 110) |
| #163, | GGACAGTGTGTATTATATGACTGAT (SEQ ID NO: 111) |
| #173, | CGGTATCCGCTACTCAGCTTGTTAA (SEQ ID NO: 112) |
| #178, | GCATTGTGGACCTGTCAACCCACTT (SEQ ID NO: 113) |

TABLE 2-continued

HPV18 Sequences Corresponding to the siRNAs Against 8 Genes (Potency Enhancer Motif, PEM, is underlined and in bold font) HPV18 - 8siRNA

| | |
|---|---|
| #182, | GGTAACACTACGCCTATAATACATT (SEQ ID NO: 114) |
| #187, | GGAATACTGACTGTAACATACCATA (SEQ ID NO: 115) |

Gene = "E4" (3418-3684)

| | |
|---|---|
| #172, | CGACACGGTATCCGCTACTCAGCTT (SEQ ID NO: 116) |
| #173, | CGGTATCCGCTACTCAGCTTGTTAA (SEQ ID NO: 112) |
| #174, | GGTATCCGCTACTCAGCTTGTTAAA (SEQ ID NO: 117) |
| #175, | CGCTACTCAGCTTGTTAAACAGCTA (SEQ ID NO: 118) |
| #178, | GCATTGTGGACCTGTCAACCCACTT (SEQ ID NO: 113) |
| #179, | CCACTTCTCGGTGCAGCTACACCTA (SEQ ID NO: 119) |
| #181, | CGGAAACTCTGTAGTGGTAACACTA (SEQ ID NO: 120) |

Gene = "E5" (3936-4157)

| | |
|---|---|
| #193, | GCCATCTGTCTGTATGTGTGCGTAT (SEQ ID NO: 121) |
| #194, | GCATGGGTATTGGTATTTGTGTATA (SEQ ID NO: 122) |
| #197, | CCCTGCCACAGCATTCACAGTATAT (SEQ ID NO: 123) |
| #198, | GCCACAGCATTCACAGTATATGTAT (SEQ ID NO: 124) |
| #199, | CCACAGCATTCACAGTATATGTATT (SEQ ID NO: 125) |
| #201, | GCCCATGTTACTATTGCATATACAT (SEQ ID NO: 126) |

Gene = "L2" (4244-5632)

| | |
|---|---|
| #206, | GCAAACGGGCTTCGGTAACTGACTT (SEQ ID NO: 127) |
| #221, | GGGTACATTCCATTGGGTGGGCGTT (SEQ ID NO: 128) |
| #230, | GGGTTTGATATAACATCTGCGGGTA (SEQ ID NO: 129) |
| #242, | CCCTACATCTGGAACACATGGGTAT (SEQ ID NO: 130) |
| #253, | CCTACCAACAAGTGTCAGTGGCTAA (SEQ ID NO: 131) |
| #262, | GCAACTATGTTTACCCGCAGCGGTA (SEQ ID NO: 132) |
| #268, | CGGAGGACAATGACTTGTTTGATAT (SEQ ID NO: 133) |

TABLE 2-continued

HPV18 Sequences Corresponding to the siRNAs Against 8 Genes
(Potency Enhancer Motif, PEM, is underlined and in bold font)
HPV18 - 8siRNA

280,   CCTCCTCTTGGGATGTGCCTGTATA
        (SEQ ID NO: 134)

Gene = "L1" (5430-7136)

288,   CCTGCCTCTACACAGTATATTGGTA
        (SEQ ID NO: 135)

307,   GGGTGCAGTTACCTGACCCAAATAA
        (SEQ ID NO: 136)

333,   GGATATGGTGCCATGGACTTTAGTA
        (SEQ ID NO: 137)

345,   CCTCTGACTCCCAGTTGTTTAATAA
        (SEQ ID NO: 138)

350,   GGTAGATACCACTCCCAGTACCAAT
        (SEQ ID NO: 139)

351,   CCACTCCCAGTACCAATTTAACAAT
        (SEQ ID NO: 140)

364,   CCAACTACTAGTTTGGTGGATACAT
        (SEQ ID NO: 141)

379,   CCACTACGTCTTCTAAACCTGCCAA
        (SEQ ID NO: 142)

TABLE 3

HPV6 and HPV11 Common Sequences Corresponding to siRNAs
(Potency Enhancer Motif, PEM, is underlined and in bold font)
siRNAs common to HPV6 & 11

Gene = "E7" (530-826)

3,     CCTGTTGCTGTGGATGTGACAGCAA
        (SEQ ID NO: 143)

Gene = "E1" (832-2781)

8,     GGACAGTGGATATGGCTATTCTGAA
        (SEQ ID NO: 144)

11,    CGAGGAAGATGGAAGCAATAGCCAA
        (SEQ ID NO: 145)

12,    GGAAGCAATAGCCAAGCGTTTAGAT
        (SEQ ID NO: 146)

Gene = "E2" (2723-3826)

14,    GGAAGTATGTTATGGCAGCACAGTT
        (SEQ ID NO: 147)

TABLE 3-continued

HPV6 and HPV11 Common Sequences Corresponding to siRNAs
(Potency Enhancer Motif, PEM, is underlined and in bold font)
siRNAs common to HPV6 & 11

Gene = "L2" (4417-5784)

15,    CCCTTTAGTCCTGTAACTCCTGCTT
        (SEQ ID NO: 148)

16,    CCTTTAGTCCTGTAACTCCTGCTTT
        (SEQ ID NO: 149)

17,    CCTGCTTTACCTACAGGCCCTGTTT
        (SEQ ID NO: 150)

Gene = "L1" (5771-7276)

21,    GGCGGCCTAGCGACAGCACAGTATA
        (SEQ ID NO: 151)

22,    GCGGCCTAGCGACAGCACAGTATAT
        (SEQ ID NO: 152)

TABLE 4 siRNAs against HPV16 E7 and hybrid CRPV E7

16E7-36:    5'-GCAUGAAUAUAUGUUAGAUUUGCAA-3'
            (SEQ ID NO: 153)

CRPE7-36:   5'-GCAUGAAUAUAUGUUGGAUCUGCA-3'
            (SEQ ID NO: 29)

16E7-37:    5'-GGACAGAGCCCAUUACAAUAUUGUA-3'
            (SEQ ID NO: 154)

CRPE7-37:   5'-GGACAGAGCCCACUACAACAUCGU-3'
            (SEQ ID NO: 30)

16E7-38:    5'-GCCCAUUACAAUACCGUAACCUUUU-3'
            (SEQ ID NO: 155)

CRPE7-38:   5'-GCCCACUACAACAUCGUGACCUUUU-3'
            (SEQ ID NO: 31)

16E7-43:    5'-GGAAGACCUGUUAAUGGGCACACUA-3'
            (SEQ ID NO: 156)

CRPE7-43:   5'-GGAAGACCUGCUGAUGGGCACCCU-3'
            (SEQ ID NO: 32)

16E7-44:    5'-CCUGUUAAUGGGCACACUAGGAAUU-3'
            (SEQ ID NO: 157)

CRPE7-44:   5'-CCUGCUGAUGGGCACCCUGGGCAU-3'
            (SEQ ID NO: 33)

16E7-45:    5'-GCACACUAGGAAUUGUGUGCCCCAU-3'
            (SEQ ID NO: 158)

CRPE7-45:   5'-GCACCCUGGGCAUCCUGUGCCCCAU-3'
            (SEQ ID NO: 34)

What is claimed is:

1. A composition comprising at least two blunt-ended siRNA molecules and a pharmaceutically acceptable carrier, wherein said siRNA molecules are selected from the group consisting of:

```
5'- GGACAGAGCCCAUUACAAUAUUGUA-3'    (SEQ ID NO: 154)
5'- GCGUACAAAGCACACACGUAGACAU-3'    (Corresponding to SEQ ID NO: 24)
5'- CGUACAAAGCACACACGUAGACAUU-3'    (Corresponding to SEQ ID NO: 25)
5'- GCACACACGUAGACAUUCGUACUUU-3'    (Corresponding to SEQ ID NO: 26)
5'- CCUGUUAAUGGGCACACUAGGAAUU-3'    (Corresponding to SEQ ID NO: 28)
5'- GGACAGAGCCCACUACAACAUCGU-3'     (SEQ ID NO: 30)
5'- GGAAGACCUGCUGAUGGGCACCCU-3'     (SEQ ID NO: 32)
5'- CCUGCUGAUGGGCACCCUGGGCAU-3'     (SEQ ID NO: 33)
5'- GCACCCUGGGCAUCCUGUGCCCCAU-3'    (SEQ ID NO: 34)
5'- CGAGCCGAACCACAACGUCACACAA-3'    (SEQ ID NO: 39)
5'- GCUCAGCAGACGACCUUCGAGCAUU-3'    (SEQ ID NO: 41) and
5'- GCUGUUUCUGAACACCCUGUCCUUU-3'    (SEQ ID NO: 42)
``` and wherein said carrier comprises a dendrimer or a histidine-lysine polymer.

2. The composition of claim 1, wherein the pharmaceutically acceptable carrier comprises a histidine-lysine polymer.

3. The composition of claim 2, wherein the siRNA molecules and the histidine-lysine polymer form a nanoparticle whose diameter is 100-400 nm.

4. The composition of claim 1, wherein the pharmaceutically acceptable carrier comprises a dendrimer.

5. A method for treating a human with an HPV infection comprising administering to said human a pharmaceutically effective amount of the composition of claim 1.

6. A method for treating a human with an HPV infection and an HIV and/or an HSV infection comprising administering to said human a pharmaceutically effective amount of the composition of claim 4.

7. A method for treating a human with an HPV infection and a fungal infection comprising administering to said human a pharmaceutically effective amount of the composition of claim 2.

8. A composition comprising at least three blunt-ended siRNA molecules and a pharmaceutically acceptable carrier, wherein said siRNA molecules are selected from the group consisting of:

```
5'- GGACAGAGCCCAUUACAAUAUUGUA-3'    (SEQ ID NO: 154)
5'- GCGUACAAAGCACACACGUAGACAU-3'    (Corresponding to SEQ ID NO: 24)
5'- CGUACAAAGCACACACGUAGACAUU-3'    (Corresponding to SEQ ID NO: 25)
5'- GCACACACGUAGACAUUCGUACUUU-3'    (Corresponding to SEQ ID NO: 26)
5'- CCUGUUAAUGGGCACACUAGGAAUU-3'    (Corresponding to SEQ ID NO: 28)
5'- GGACAGAGCCCACUACAACAUCGU-3'     (SEQ ID NO: 30)
5'- GGAAGACCUGCUGAUGGGCACCCU-3'     (SEQ ID NO: 32)
5'- CCUGCUGAUGGGCACCCUGGGCAU-3'     (SEQ ID NO: 33)
5'- GCACCCUGGGCAUCCUGUGCCCCAU-3'    (SEQ ID NO: 34)
5'- CGAGCCGAACCACAACGUCACACAA-3'    (SEQ ID NO: 39)
5'- GCUCAGCAGACGACCUUCGAGCAUU-3'    (SEQ ID NO: 41) and
5'- GCUGUUUCUGAACACCCUGUCCUUU-3'    (SEQ ID NO: 42)
``` and wherein said carrier comprises a dendrimer or a histidine-lysine polymer.

9. The composition of claim 8, wherein the pharmaceutically acceptable carrier comprises a dendrimer.

10. The composition of claim 8, wherein the pharmaceutically acceptable carrier comprises a histidine-lysine polymer.

11. The composition of claim 8, wherein said composition comprises three siRNA molecules at a ratio of 1:1:1, 1:1.5:0.5, or 0.5:0.5:2.

12. A method of treating a human with an HPV infection comprising administering to said human a pharmaceutically effective amount of the composition of claim 8.

13. A method of treating a human with an HPV infection and with an HIV and/or HSV infection comprising administering to said human a pharmaceutically effective amount of the composition of claim 9.

14. A method of treating a human with an HPV infection and with a fungal infection comprising administering to said human a pharmaceutically effective amount of the composition of claim 10.

15. A nanoparticle comprising the siRNA molecules of claim 1, a pharmaceutically acceptable carrier, and a targeting ligand.

16. A nanoparticle comprising the siRNA molecules of claim 8, a pharmaceutically acceptable carrier, and a targeting ligand.

17. The composition of claim 10, wherein the siRNA molecules and the histidine-lysine polymer form a nanoparticle whose diameter is 100-400 nm.

18. The nanoparticle of claim 15, wherein the targeting ligand comprises an RGD peptide, an RVD peptide, or a FROP peptide.

19. A composition comprising at least two blunt-ended siRNA molecules and a pharmaceutically acceptable carrier, wherein said siRNA molecules are selected from the group consisting of:

5'-CCUGUUAAUGGGCACACUAGGAAUU-3' (Corresponding to SEQ ID NO: 28) and

5'-CGAGCCGAACCACAACGUCACACAA-3' (SEQ ID NO: 39), and wherein said carrier comprises a dendrimer or a histidine-lysine polymer.

20. The composition of claim 19, wherein the pharmaceutically acceptable carrier comprises a histidine-lysine polymer.

21. The composition of claim 20, wherein the siRNA molecules and the histidine-lysine polymer form a nanoparticle whose diameter is 100-400 nm.

22. The composition of claim 19, wherein the pharmaceutically acceptable carrier comprises a dendrimer.

23. A method for treating a human with an HPV infection comprising administering to said human a pharmaceutically effective amount of the composition of claim 19.

24. A method for treating a human with an HPV infection and an HIV and/or an HSV infection comprising administering to said human a pharmaceutically effective amount of the composition of claim 22.

25. A method for treating a human with an HPV infection and a fungal infection comprising administering to said human a pharmaceutically effective amount of the composition of claim 20.

26. A nanoparticle comprising the siRNA molecules of claim 19, a pharmaceutically acceptable carrier, and a targeting ligand.

27. The nanoparticle of claim 26, wherein the targeting ligand comprises an RGD peptide, an RVD peptide, or a FROP peptide.

* * * * *